US 6,515,004 B1
United States Patent
Misra et al.

(10) Patent No.: US 6,515,004 B1
(45) Date of Patent: *Feb. 4, 2003

(54) N-[5-[[[5-ALKYL-2-OXAZOLYL]METHYL]THIO]-2-THIAZOLYL]-CARBOXAMIDE INHIBITORS OF CYCLIN DEPENDENT KINASES

(75) Inventors: Raj N. Misra, Hopewell, NJ (US); Hai-Yun Xiao, Princeton, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/727,957

(22) Filed: Dec. 1, 2000

Related U.S. Application Data

(63) Continuation-in-part of application No. 09/616,627, filed on Jul. 26, 2000, which is a continuation-in-part of application No. 09/464,511, filed on Dec. 15, 1999.

(51) Int. Cl.$^7$ .................... C07D 417/12; A61K 31/425
(52) U.S. Cl. .................... 514/369; 548/184; 548/185
(58) Field of Search ................ 548/184, 185; 514/369

(56) References Cited

FOREIGN PATENT DOCUMENTS

| EP | 0082498 B1 | 11/1989 |
| EP | 0625307 A1 | 11/1994 |
| EP | 0412404 B1 | 1/1996 |
| WO | WO 95/24403 | 9/1995 |
| WO | WO 96/17850 | 6/1996 |
| WO | WO 96/30370 | 10/1996 |
| WO | WO 97/29111 | 8/1997 |
| WO | WO 99/21845 | 5/1999 |
| WO | WO 99/24416 | 5/1999 |
| WO | WO 00/26202 | 5/2000 |
| WO | WO 01/44217 | 6/2000 |
| WO | WO 01/44242 | 6/2000 |
| WO | WO 01/44241 | 4/2001 |

OTHER PUBLICATIONS

T. Ogino et al., "Discovery of FR1115092: A Novel Antinephritic Agent"; Bioorg. & Med. Chem. Lett. 8 (1998) 75–80.

K. Tsuji et al., "Synthesis and Effects of Novel Thiazole Derivatives Against Thrombocytopenia"; Bioorg. & Med. Chem. Lett. 8 (1998) 2473–2478.

Baddi et al., "Synthesis and Antimicrobial Activity of Some Ethyl–2–amino/acetamido–5–arythiothiazole–4–carboxylates and their sulphones: An attempted synthesis of 2–amino/acetamido[1]benzothiopyrano[3,2–d]thiazol–9(H)–ones", Indian J. Chem. 35B (1996) 233–237.

Smith et al., Heterocycles, vol. 37, No. 3, pp. 1865–1872, 1994.

Bellavita et al., Ann. Chim. (Rome) 41, (1951) 194–198.

J. Am. Chem. Soc., vol. LXXI (1949) 4007–4010.

Behringer et al., Ann. Chem. 650 (1961) 179.

Scott et al., Applied Microbiology, vol. 10, pp. 211–216, 1962.

Hall et al., Journal of Heterocyclic Chemistry, vol. 29, No. 5, pp. 1245–1273, 1992.

Ganellin et al., Journal of Medicinal Chemistry, vol. 38, No. 17, pp. 3342–3350, 1995.

Primary Examiner—Robert Gerstl
(74) Attorney, Agent, or Firm—Rena Patel

(57) ABSTRACT

The present invention describes compounds of formula I:

(1)

and enantiomers, diastereomers and pharmaceutically acceptable salts thereof.

The formula I compounds are protein kinase inhibitors and are useful in the treatment of proliferative diseases, for example, cancer, inflammation and arthritis. They may also be useful in the treatment of Alzheimer's disease, chemotherapy-induced alopecia, and cardiovascular disease.

59 Claims, No Drawings

N-[5-[[[5-ALKYL-2-OXAZOLYL]METHYL]THIO]-2-THIAZOLYL]-CARBOXAMIDE INHIBITORS OF CYCLIN DEPENDENT KINASES

RELATED APPLICATION

This application is a continuation-in-part of U.S. patent application Ser. No. 09/616,627, filed Jul. 26, 2000, which is a continuation-in-part application of U.S. application Ser. No. 09/464,511, filed on Dec. 15, 1999, both of which are incorporated by reference in their entirety.

BRIEF DESCRIPTION OF THE INVENTION

The present invention is directed to compounds of formula I

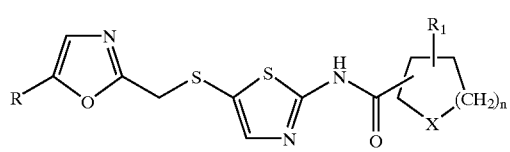

(1)

and enantiomers, diastereomers and pharmaceutically acceptable salts thereof wherein R is alkyl;

$R_1$ is hydrogen or alkyl;

X is $NR_2$ or $CHNR_2R_3$;

$R_2$ and $R_3$ are each independently hydrogen, alkyl, substituted alkyl, cycloalkyl or substituted cycloalkyl; and n is 0, 1, 2 or 3.

The compounds of formula I are particularly useful as potent, protein kinase inhibitors and are useful in the treatment of proliferative diseases, for example, cancer, inflammation and arthritis. They may also be useful in the treatment of Alzheimer's disease, chemotherapy-induced alopecia, and cardiovascular disease.

DESCRIPTION OF THE INVENTION

The present invention provides for compounds of formula I, pharmaceutical compositions employing such compounds, and for methods of using such compounds.

Listed below are definitions of various terms used to describe the compounds of the instant invention. These definitions apply to the terms as they are used throughout the specification (unless they are otherwise limited in specific instances) either individually or as part of a larger group.

The term "alkyl" or "alk" refers to a monovalent alkane (hydrocarbon) derived radical containing from 1 to 12, preferably 1 to 6, and more preferably 1 to 4, carbon atoms unless otherwise defined. An alkyl group is an optionally substituted straight, branched or cyclic saturated hydrocarbon group. When substituted, alkyl groups may be substituted with up to four substituent groups, $R_4$ as defined, at any available point of attachment. When the alkyl group is said to be substituted with an alkyl group, this is used interchangeably with "branched alkyl group". Exemplary unsubstituted such groups include methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, and the like. Exemplary substituents may include, but are not limited to, one or more of the following groups: halo (such as F, Cl, Br or I), haloalkyl (such as $CCl_3$ or $CF_3$), alkoxy, alkylthio, hydroxy, carboxy, alkylcarbonyl, alkyloxycarbonyl, alkylcarbonyloxy, amino, carbamoyl, urea, amidinyl, or thiol.

Cycloalkyl is a specie of alkyl containing from 3 to 15 carbon atoms, without alternating or resonating double bonds between carbon atoms. It may contain from 1 to 4 rings. Exemplary unsubstituted such groups include cyclopropyl, cyclobutyl, cyclopentyl, cyclohexyl, etc. Exemplary substituents include one or more of the following groups: halogen, alkyl, alkoxy, alkyl hydroxy, amino, nitro, cyano, thiol and/or alkylthio.

The terms "alkoxy" or "alkylthio", as used herein, denote an alkyl group as described above bonded through an oxygen linkage (—O—) or a sulfur linkage (—S—), respectively.

The term "alkyloxycarbonyl", as used herein, denotes an alkoxy group bonded through a carbonyl group. An alkoxycarbonyl radical is represented by the formula: —$C(O)OR_5$, where the $R_5$ group is a straight or branched $C_{1-6}$ alkyl group.

The term "alkylcarbonyl" refers to an alkyl group bonded through a carbonyl group.

The term "alkylcarbonyloxy", as used herein, denotes an alkylcarbonyl group which is bonded through an oxygen linkage.

Pharmaceutically acceptable salts of compounds of formula I which are suitable for use in the methods and compositions of the present invention include, but are not limited to, salts formed with a variety of organic and inorganic acids such as hydrogen chloride, hydroxymethane sulfonic acid, hydrogen bromide, hydrogen iodide, methanesulfonic acid, sulfuric acid, acetic acid, trifluoroacetic acid, maleic acid, fumaric acid, benzenesulfonic acid, toluenesulfonic acid and various others, e.g., nitrates, phosphates, borates, tartrates, citrates, succinates, benzoates, ascorbates, salicylates, and the like. These salts include racemic forms as well as enantiomers, and diastereomers (such as, for example, D-tartrate and L-tartrate salts). In addition, pharmaceutically acceptable salts of compounds of formula I may be formed with alkali metals such as sodium, potassium and lithium; alkaline earth metals such as calcium and magnesium; organic bases such as dicyclohexylamine, tributylamine, and pyridines, and the like; and amino acids such as arginine, lysine and the like.

All stereoisomers of the compounds of the instant invention are contemplated, either in admixture or in pure or substantially pure form. The definition of the compounds according to the invention embraces all possible stereoisomers and their mixtures. It very particularly embraces the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates by conventional methods, such as, for example, salt formation with an optically active acid followed by crystallization.

All configurational isomers of compounds of the present invention are contemplated, either in admixture or in pure or substantially pure form. The definition of compounds of the present invention very particularly embraces both cis and trans isomers of cycloalkyl rings.

In the context of the present invention, the definition of compounds of the present invention includes the free base, enantiomers, diastereomers as well as pharmaceutically acceptable salts. Examples of such pharmaceutically acceptable salts include, but are not limited to, hydrochloride, dihydrochloride, sulfate, trifluoroacetate, mixture of trifluoroacetate and hydrochloride, tartrate, fumarate, succinate, maleate, citrate, methanesulfonate, bromate and iodate salts. Also included are salts formed with other organic and inorganic acids such as hydroxymethane sulfonic acid, acetic acid, benzenesulfonic acid, toluenesulfonic acid and various others, e.g., nitrates, phosphates, borates, benzoates, ascorbates, salicylates, and the like. These salts include racemic forms as well as enantiomers and diastereomers (such as, for example, D-tartrate and L-tartrate salts). In addition, pharmaceutically acceptable salts of the formula I compounds may be formed with alkali metals such as sodium, potassium and lithium; alkaline earth metals such as calcium and magnesium; organic bases such as dicyclohexylamine, tributylamine, and pyridines, and the like; and amino acids such as arginine, lysine and the like.

It should be understood that solvates (e.g. hydrates) of the compounds of formula I are also within the scope of the present invention. Methods of solvation are generally known in the art. Accordingly, the compounds of the instant invention may be in the free or hydrate form, and may be obtained by methods exemplified by the following schemes.

Compounds of formula I may generally be prepared, as shown in Scheme 1, by reacting an amine of formula II with a carboxylic acid of formula III in the presence of 1-(3-dimethylaminopropyl)-3-ethylcarbodiimide hydrochloride and a base.

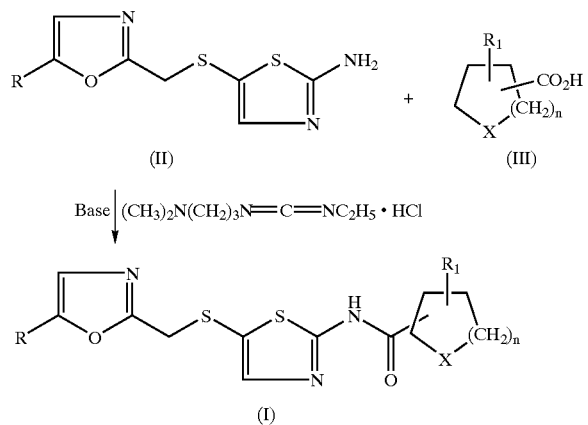

Formula I compounds wherein X is $NR_2$ and $R_2$ is hydrogen may be prepared, as shown in Scheme 2, by reacting an amine of formula II with a carboxylic acid of formula IV in the presence of 1-(3-dimethylaminopropyl)-3-ethylcarbodiimide hydrochloride and a base to form an N-protected compound of formula V, and deprotecting the formula V compound with acid.

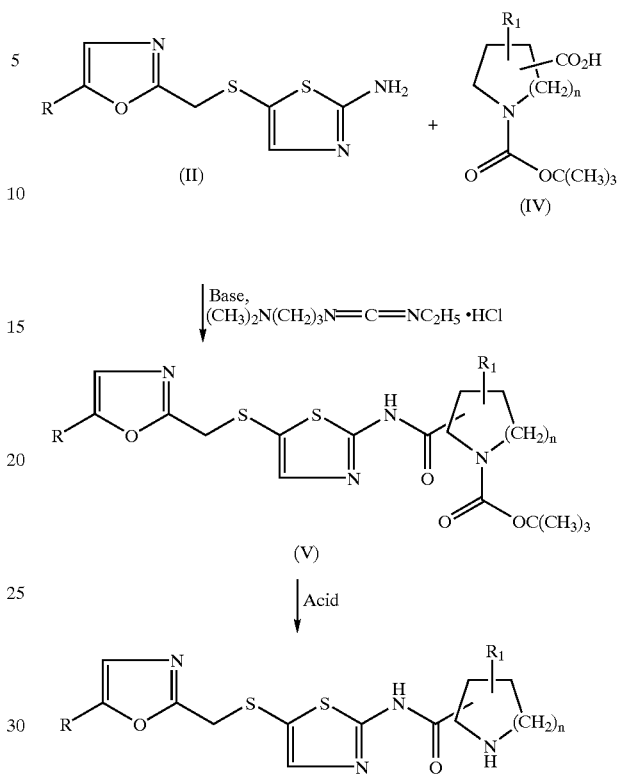

Compounds of formula I wherein X is $NR_2$ and $R_2$ is 2,3-dihydroxypropyl may be prepared, as shown in Scheme 3, by reacting a compound of formula I wherein X is NR2 and $R_2$ is hydrogen with glyceraldehyde in the presence of a reducing agent such as sodium triacetoxyborohydride and an alcohol such as methanol.

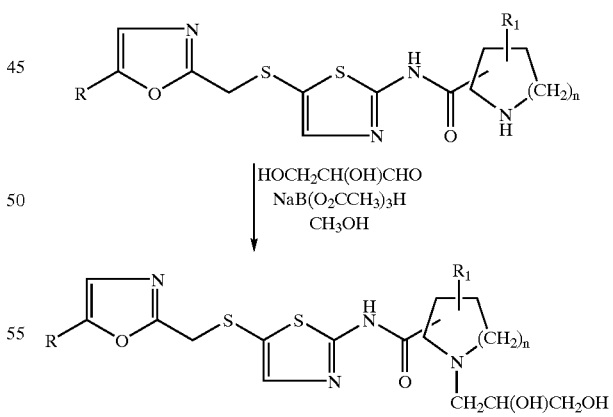

Formula I compounds wherein X is $NR_2$ and $R_2$ is 2-hydroxyethyl may be prepared, as shown in Scheme 4, by reacting a compound of formula I wherein X is $NR_2$ and $R_2$ is hydrogen with a 2-(bromoethoxy)trialkylsilane of formula VI to form an intermediate compound of formula VII, and deprotecting the formula VI compound with an acid such as hydrogen fluoride.

Scheme 4

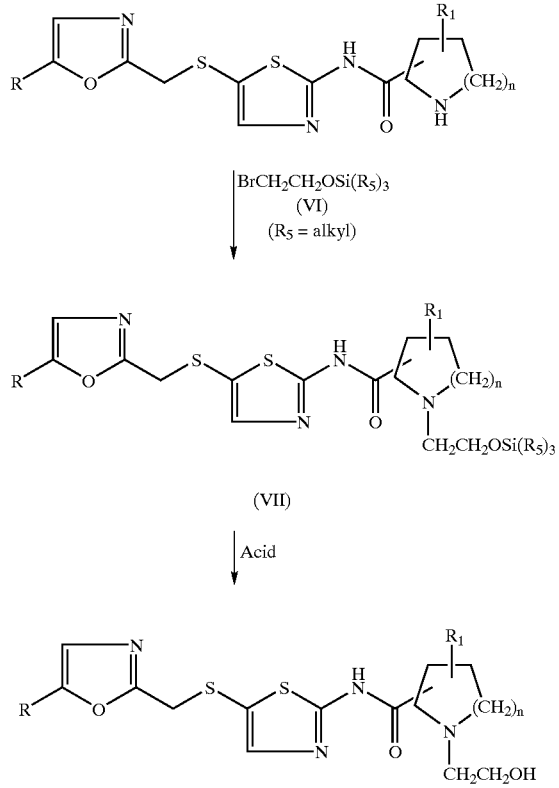

Scheme 5

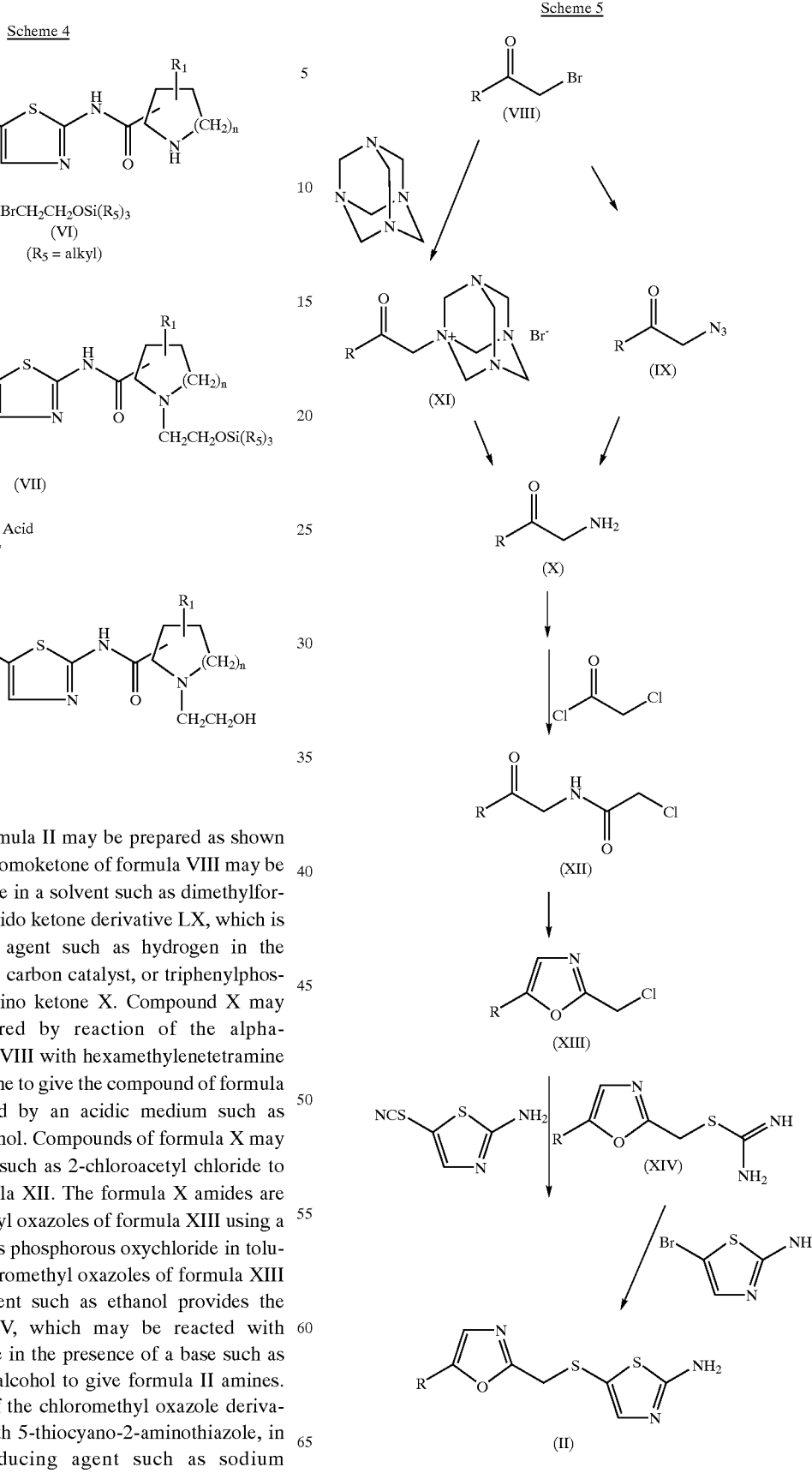

Starting amines of formula II may be prepared as shown in Scheme 5. An alpha-bromoketone of formula VIII may be reacted with sodium azide in a solvent such as dimethylformamide to provide the azido ketone derivative LX, which is reduced by a reducing agent such as hydrogen in the presence of palladium on carbon catalyst, or triphenylphosphine to provide the amino ketone X. Compound X may alternatively be prepared by reaction of the alpha-bromoketone of formula VIII with hexamethylenetetramine in a solvent such as acetone to give the compound of formula XI, which is hydrolyzed by an acidic medium such as hydrochloric acid in ethanol. Compounds of formula X may be acylated by an agent such as 2-chloroacetyl chloride to provide amides of formula XII. The formula X amides are cyclized to 2-chloromethyl oxazoles of formula XIII using a dehydrating agent such as phosphorous oxychloride in toluene. Reaction of the chloromethyl oxazoles of formula XIII with thiourea in a solvent such as ethanol provides the thiourea derivatives XIV, which may be reacted with 5-bromo-2-aminothiazole in the presence of a base such as potassium hydroxide in alcohol to give formula II amines. Alternatively, reaction of the chloromethyl oxazole derivatives of formula XIII with 5-thiocyano-2-aminothiazole, in the presence of a reducing agent such as sodium borohydride, provides compounds of formula II.

Preferred compounds of formula I are those wherein:
R is alkyl;
R₁ is hydrogen;
X is NR₂ or CHNR₂R₃;
R₂ and R₃ are each independently hydrogen, alkyl, substituted alkyl or cycloalkyl; and
n is 2.

A first group of more preferred compounds of the present invention are those of formula Ia

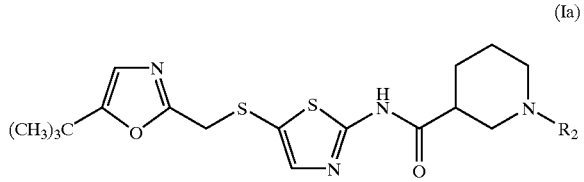

(Ia)

and enantiomers, diastereomers and pharmaceutically acceptable salts thereof wherein R₂ is hydrogen, alkyl, substituted alkyl or cycloalkyl.

A second group of more preferred compounds of this invention are those of formula Ib

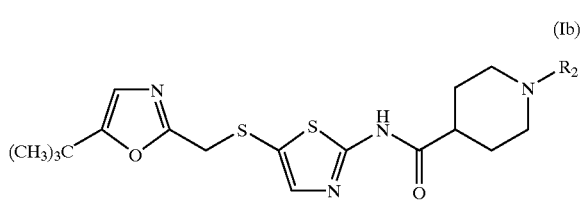

(Ib)

and enantiomers, diastereomers and pharmaceutically acceptable salts thereof wherein R₂ is hydrogen, alkyl, substituted alkyl or cycloalkyl.

A third group of more preferred compounds of the present invention are those of formula Ic

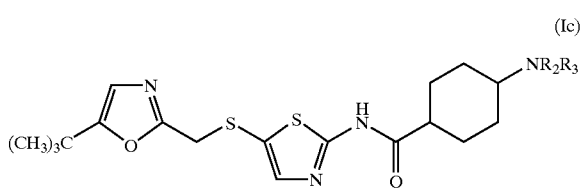

(Ic)

and enantiomers, diastereomers and pharmaceutically acceptable salts thereof wherein R₂ and R₃ are each independently hydrogen, alkyl, substituted alkyl or cycloalkyl.

Formula I compounds particularly useful in the methods of this invention include:

N-[5-[[[5-(1,1-dimethylethyl)-2-oxazolyl]methyl]thio]-2-thiazolyl]-4-piperidinecarboxamide;
(±)-N-[5-[[[5-(1,1-dimethylethyl)-2-oxazolyl]methyl]thio]-2-thiazolyl]-3-piperidinecarboxamide;
(±)-1-(2,3-dihydroxypropyl)-N-[5-[[[5-(1,1-dimethylethyl)-2-oxazolyl]methyl]thio]-2-thiazolyl]-4-piperidinecarboxamide;
N-[5-[[[5-(1,1-dimethylethyl)-2-oxazolyl]methyl]thio]-2-thiazolyl]-1-(1-methylethyl)-4-piperidinecarboxamide;
1-cyclopropyl-N-[5-[[[5-(1,1-dimethylethyl)-2-oxazolyl]methyl]thio]-2-thiazolyl]-4-piperidinecarboxamide;
N-[5-[[[5-(1,1-dimethylethyl)-2-oxazolyl]methyl]thio]-2-thiazolyl]-1-(2-hydroxyethyl)-4-piperidinecarboxamide;
(R)-N-[5-[[[5-(1,1-dimethylethyl)-2-oxazolyl]methyl]thio]-2-thiazolyl]-3-piperidinecarboxamide;
(S)-N-[5-[[[5-(1,1-dimethylethyl)-2-oxazolyl]methyl]thio]-2-thiazolyl]-3-piperidinecarboxamide;
cis-4-amino-N-[5-[[[5-(1,1-dimethylethyl)-2-oxazolyl]methyl]thio]-2-thiazolyl]cyclohexylcarboxamide; and
trans-4-amino-N-[5-[[[5-(1,1-dimethylethyl)-2-oxazolyl]methyl]thio]-2-thiazolyl]cyclohexylcarboxamide; and pharmaceutically acceptable salts thereof.

The present invention also includes methods based upon the pharmacological properties of the compounds of the invention. It should be noted that, in the context of the methods of the present invention, the compounds of the invention, or compounds of formula I, refer to the free base, enantiomers, diastereomers as well as pharmaceutically acceptable salts. Examples of such pharmaceutically acceptable salts include, but are not limited to, hydrochloride, dihydrochloride, sulfate, trifluoroacetate, mixture of trifluoroacetate and hydrochloride, tartrate, fumarate, succinate, maleate, citrate, methanesulfonate, bromate and iodate salts. Also included are salts formed with other organic and inorganic acids such as hydroxymethane sulfonic acid, acetic acid, benzenesulfonic acid, toluenesulfonic acid and various others, e.g., nitrates, phosphates, borates, benzoates, ascorbates, salicylates, and the like. These salts include racemic forms as well as enantiomers and diastereomers (such as, for example, D-tartrate and L-tartrate salts). In addition, pharmaceutically acceptable salts of compounds of formula I may be formed with alkali metals such as sodium, potassium and lithium; alkaline earth metals such as calcium and magnesium; organic bases such as dicyclohexylamine, tributylamine, and pyridines, and the like; and amino acids such as arginine, lysine and the like.

The compounds according to the invention have pharmacological properties; in particular, the compounds of formula I are inhibitors of protein kinases such as the cyclin dependent kinases (cdks), for example, cdc2 (cdk1), cdk2, cdk3, cdk4, cdk5, cdk6, cdk7 and cdk8. The novel compounds of formula I are expected to be useful in the therapy of proliferative diseases such as cancer, inflammation, arthritis, Alzheimer's disease and cardiovascular disease. These compounds may also be useful in the treatment of topical and systemic fungal infections.

More specifically, the compounds of formula I are useful in the treatment of a variety of cancers, including (but not limited to) the following:

carcinoma, including that of the bladder, breast, colon, kidney, liver, lung, ovary, pancreas, stomach, cervix, thyroid, prostate, and skin;
hematopoietic tumors of lymphoid lineage, including acute lymphocytic leukemia, B-cell lymphoma, and Burkett's lymphoma;
hematopoietic tumors of myeloid lineage, including acute and chronic myelogenous leukemias and promyelocytic leukemia;
tumors of mesenchymal origin, including fibrosarcoma and rhabdomyosarcoma; and
other tumors, including melanoma, seminoma, teratocarcinoma, osteosarcoma, neuroblastoma and glioma.

Due to the key role of cdks in the regulation of cellular proliferation in general, inhibitors could act as reversible cytostatic agents which may be useful in the treatment of any disease process which features abnormal celluar proliferation, e.g., neuro-fibromatosis, atherosclerosis, pulmonary fibrosis, arthritis, psoriasis, glomerulonephritis, restenosis following angioplasty or vascular surgery, hypertrophic scar formation, inflammatory bowel disease, transplantation rejection, angiogenesis, and endotoxic shock.

Compounds of formula I may also be useful in the treatment of Alzheimer's disease, as suggested by the recent finding that cdk5 is involved in the phosphorylation of tau protein (*J. Biochem,* 117, 741–749 (1995)).

Compounds of formula I may also act as inhibitors of other protein kinases, e.g., protein kinase C, her2, raf1, MEK1, MAP kinase, EGF receptor, PDGF receptor, IGF receptor, PI3 kinase, wee 1 kinase, Src, Ab1, VEGF, and lck, and thus be effective in the treatment of diseases associated with other protein kinases.

Compounds of formula I also induce or inhibit apoptosis, a physiological cell death process critical for normal development and homeostasis. Alterations of apoptotic pathways contribute to the pathogenesis of a variety of human diseases. Compounds of formula I, as modulators of apoptosis, will be useful in the treatment of a variety of human diseases with abberations in apoptosis including cancer (particularly, but not limited to, follicular lymphomas, carcinomas with p53 mutations, hormone dependent tumors of the breast, prostate and ovary, and precancerous lesions such as familial adenomatous polyposis), viral infections (including, but not limited to, herpesvirus, poxvirus, Epstein-Barr virus, Sindbis virus and adenovirus), autoimmune diseases (including, but not limited to, systemic lupus, erythematosus, immune mediated glomerulonephritis, rheumatoid arthritis, psoriasis, inflammatory bowel diseases, and autoimmune diabetes mellitus), neurodegenerative disorders (including, but not limited to, Alzheimer's disease, AIDS-related dementia, Parkinson's disease, amyotrophic lateral sclerosis, retinitis pigmentosa, spinal muscular atrophy and cerebellar degeneration), AIDS, myelodysplastic syndromes, aplastic anemia, ischemic injury associated myocardial infaretions, stroke and reperfusion injury, arrhythmia, atherosclerosis, toxin-induced or alcohol induced liver diseases, hematological diseases (including, but not limited to, chronic anemia and aplastic anemia), degenerative diseases of the muscu-loskeletal system (including, but not limited to, osteoporosis and arthritis), aspirin-sensitive rhinosinusitis, cystic fibrosis, multiple sclerosis, kidney diseases, and cancer pain.

In addition, the formula I compounds may be used for treating chemotherapy-induced alopecia, chemotherapy-induced thrombocytopenia, chemotherapy-induced leukopenia or mucocitis. In the treatment of chemotherapy-induced alopecia, the formula I compound is preferably topically applied in the form of a medicament such as a gel, solution, dispersion or paste.

The compounds of this invention may be used in combination with known anti-cancer treatments such as radiation therapy or with cytostatic and cytotoxic agents including, but not limited to, microtuble-stabilizing agents, microtuble-disruptor agents, alkylating agents, anti-metabolites, epidophyllotoxin, an antineoplastic enzyme, a topoisomerase inhibitor, procarbazine, mitoxantrone, platinum coordination complexes, biological response modifiers, growth inhibitors, hormonal/anti-hormonal therapeutic agents, haematopoietic growth factors, and the like.

Classes of anti-cancer agents which may be used in combination with the formula I compounds of this invention include, but are not limited to, the anthracycline family of drugs, the vinca drugs, the mitomycins, the bleomycins, the cytotoxic nucleosides, the taxanes, the epothilones, discodermolide, the pteridine family of drugs, diynenes, aromatase inhibitors, and the podophyllotoxins. Particluar members of those classes include, for example, paclitaxel, docetaxel, 7-O-methylthiomethylpaclitaxel (disclosed in U.S. Pat. No. 5,646,176), 3'-tert-butyl-3'-N-tert-butyloxycarbonyl-4-deacetyl-3'-dephenyl-3'-N-debenzoyl-4-O-methoxycarbonyl-paclitaxel (disclosed in U.S. Ser. No. 60/179,965) filed on Feb. 3, 2000 which is incorporated herein by reference thereto), C-4 methyl carbonate paclitaxel (disclosed in WO 94/14787), epothilone A, epothilone B, epothilone C, epothilone D, desoxyepothilone A, desoxyepothilone B, [1S-[1R*,3R*(E),7R*,10S*,11R*,12R*,16S*]]-7,11-dihydroxy-8,8,10,12,16-pentamethyl-3-[1-methyl-2-(2-methyl-4-thiazolyl)ethenyl]-4-aza-17-oxabicyclo[14.1.0]heptadecane-5,9-dione (disclosed in WO 99/02514), [1S-[R*,3R*(E),7R*,10S*,11R*,12R*,16S*]]-3-[2-[2-(aminomethyl)-4-thiazolyl]-1-methylethenyl]-7,11-dihydroxy-8,8,10,12,16-pentamethyl-4,17-dioxabicyclo [14.1.0]heptadecane-5,9-dione (disclosed in U.S. Ser. No. 09/506,481 filed on Feb. 17, 2000 which is incorporated herein by reference thereto), doxorubicin, carminomycin, daunorubicin, aminopterin, methotrexate, methopterin, dichloro-methotrexate, mitomycin C, porfiromycin, 5-fluorouracil, 6-mercaptopurine, gemcitabine, cytosine arabinoside, podophyllotoxin or podophyllotoxin derivatives such as etoposide, etoposide phosphate or teniposide, melphalan, vinblastine, vincristine, leurosidine, vindesine, leurosine, and the like. Other useful anti-cancer agents which may be used in combination with the compounds of the present invention include, but are not limited to, estramustine, cisplatin, carboplatin, cyclophosphamide, bleomycin, tamoxifen, ifosamide, melphalan, hexamethyl melamine, thiotepa, cytarabin, idatrexate, trimetrexate, dacarbazine, L-asparaginase, camptothecin, CPT-11, topotecan, ara-C, bicalutamide, flutamide, leuprolide, pyridobenzoindole derivatives, interferons, interleukins, and the like. In addition, the compounds of this invention may be used in combination with inhibitors of famesyl protein transferase such as those described in U.S. Pat No. 6,011,029; anti-angiogenic agents such as angiostatin and endostatin; kinase inhibitors such as her2 specific antibodies; and modulators of p53 transactivation.

If formulated as a fixed dose, such combination products employ the compounds of this invention within the dosage range described below and the other pharmaceutically active agent within its approved dosage range. Compounds of formula I may be used sequentially, in any order, with known anti-cancer or cytotoxic agents when a combination formulation is inappropriate.

The present invention also provides pharmaceutical compositions which comprise a compound of this invention and a pharmaceutically acceptable carrier. It should be noted that, in the context of the pharmaceutical compositions of the present invention, the compounds of the invention, or compounds of formula I, refer to the free base, enantiomers, diastereomers as well as pharmaceutically acceptable salts. Examples of such pharmaceutically acceptable salts include, but are not limited to, hydrochloride, dihydrochloride, sulfate, trifluoroacetate, mixture of trifluoroacetate and hydrochloride, tartrate, fumarate, succinate, maleate, citrate, methanesulfonate, bromate and iodate salts. Also included are salts formed with other organic and inorganic acids such as hydroxymethane sulfonic acid, acetic acid, benzenesulfonic acid, toluenesulfonic acid and various others, e.g., nitrates, phosphates, borates, benzoates, ascorbates, salicylates, and the like. These salts include racemic forms as well as enantiomers and diastereomers (such as, for example, D-tartrate and L-tartrate salts). In addition, pharmaceutically acceptable salts of compounds of formula I may be formed with alkali metals such as sodium, potassium and lithium; alkaline earth metals such as calcium and magnesium; organic bases such as dicyclohexylamine, tributylamine, and pyridines, and the like; and amino acids such as arginine, lysine and the like.

The pharmaceutical compositions of the present invention may further comprise one or more pharmaceutically acceptable additional ingredient(s) such as alum, stabilizers, antimicrobial agents, buffers, coloring agents, flavoring agents, and the like. The compounds and compositions of this invention may be administered orally or parenterally including the intravenous, intramuscular, intraperitoneal, subcutaneous, rectal and topical routes of administration.

For oral use, the compounds and compositions of this invention may be administered, for example, in the form of tablets or capsules, or as solutions or suspensions. In the case of tablets for oral use, carriers which are commonly used include lactose and corn starch, and lubricating agents such as magnesium stearate are commonly added. For oral administration in capsule form, useful carriers include lactose and corn starch. When aqueous suspensions are used for oral administration, emulsifying and/or suspending agents are commonly added. In addition, sweetening and/or flavoring agents may be added to the oral compositions. For intramuscular, intraperitoneal, subcutaneous and intravenous use, sterile solutions of the active ingredient(s) are usually employed, and the pH of the solutions should be suitably adjusted and buffered. For intravenous use, the total concentration of the solute(s) should be controlled in order to render the preparation isotonic.

Daily dosages for human administration of the compounds of this invention will normally be determined by the prescribing physician with the dosages generally varying according to the age, weight, route of administration, and response of the individual patient, as well as the severity of the patient's symptoms. A formula I compound of this invention is preferably administered to humans in an amount from about 0.001 mg/kg of body weight to about 100 mg/kg of body weight per day, more preferably from about 0.01 mg/kg of body weight to about 50 mg/kg of body weight per day, and most preferably from about 0.1 mg/kg of body weight to about 20 mg/kg of body weight per day.

cdc2/cyclin B1 Kinase Assay cdc2/cyclin B 1 kinase activity was determined by monitoring the incorporation of $^{32}P$ into histone HI. The reaction consisted of 50 ng baculovirus expressed GST-cdc2, 75 ng baculovirus expressed GST-cyclin B1, 1 μg histone HI (Boehringer Mannheim), 0.2 μCi of $^{32}P$ γ-ATP and 25 μM ATP in kinase buffer (50 mM Tris, pH 8.0, 10 mM MgCl$_2$, 1 mM EGTA, 0.5 mM DTT). The reaction was incubated at 30° C. for 30 minutes and then stopped by the addition of cold trichloroacetic acid (TCA) to a final concentration of 15% and incubated on ice for 20 minutes. The reaction was harvested onto GF/C unifilter plates (Packard) using a Packard Filtermate Universal harvester, and the filters were counted on a Packard TopCount 96-well liquid scintillation counter (Marshak, D. R., Vanderberg, M. T., Bae, Y. S., Yu, I. J., *J. of Cellular Biochemistry*, 45, 391–400 (1991), incorporated by reference herein).

cdk2/cyclin E Kinase Assay cdk2/cyclin E kinase activity was determined by monitoring the incorporation of $^{32}P$ into the retinoblastoma protein. The reaction consisted of 2.5 ng baculovirus expressed GST-cdk2/cyclin E, 500 ng bacterially produced GST-retinoblastoma protein (aa 776–928), 0.2 μCi $^{32}P$ γ-ATP and 25 μM ATP in kinase buffer (50 mM Hepes, pH 8.0, 10 mM MgCl$_2$, 5 mM EGTA, 2 mM DTT). The reaction was incubated at 30° C. for 30 minutes and then stopped by the addition of cold trichloroacetic acid (TCA) to a final concentration of 15% and incubated on ice for 20 minutes. The reaction was harvested onto GF/C unifilter plates (Packard) using a Packard Filtermate Universal harvester, and the filters were counted on a Packard TopCount 96-well liquid scintillation counter.

cdk 4/cyclin D1 Kinase Activity cdk4/cyclin D1 kinase activity was determined by monitoring the incorporation of $^{32}P$ in to the retinoblastoma protein. The reaction consisted of 165 ng baculovirus expressed as GST-cdk4, 282 ng bacterially expressed as S-tag cyclin D1, 500 ng bacterially produced GST-retinoblastoma protein (aa 776–928), 0.2 μCi $^{32}P$ γ-ATP and 25 μM ATP in kinase buffer (50 mM Hepes, pH 8.0, 10 mM MgCl$_2$, 5 mM EGTA, 2 mM DTT). The reaction was incubated at 30° C. for 1 hour and then stopped by the addition of cold trichloroacetic acid (TCA) to a final concentration of 15% and incubated on ice for 20 minutes. The reaction was harvested onto GF/C unifilter plates (Packard) using a Packard Filtermate Universal harvester, and the filters were counted on a Packard TopCount 96-well liquid scintillation counter (Coleman, K. G., Wautlet, B. S., Morissey, D, Mulheron, J. G., Sedman, S., Brinkley, P., Price, S., Webster, K. R. (1997) Identification of CDK4 Sequences involved in cyclin D, and p16 binding. *J. Biol Chem.* 272,30:18869–18874, incorporated by reference herein).

In order to facilitate a further understanding of the invention, the following examples are presented primarily for the purpose of illustrating more specific details thereof. The scope of the invention should not be deemed limited by the examples, but encompasses the entire subject matter defined in the claims.

EXAMPLE 1

Preparation of N-[5-[[[5-(1,1-Dimethylethyl)-2-oxazolyl]methyl]thio]-2-thiazolyl]-4-piperidinecarboxamide

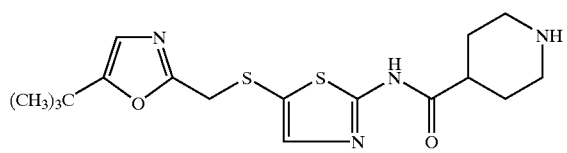

A. N-(3,3-Dimethyl-2-butanonyl) hexamethylenetetraminium bromide

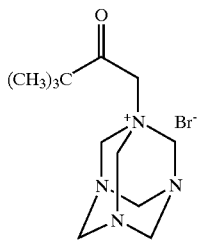

1-Bromopinacolone (179.05 g, 1 mol, 1 eq) was combined in 2 L of acetone with hexamethylenetetramine (154.21 g, 1.1 mol, 1.1 eq). The reaction mixture was stirred under $N_2$ at rt for 26 h. The resulting slurry was filtered. The filter cake was washed with ether (3×50 mL) and dried in vacuo at 50° C. overnight to provide 330 g (100%) of N-(3,3-dimethyl-2-butanonyl)hexamethylenetetraminium bromide containing 7% hexamethylenetetramine. HPLC R.T.=0.17 min (Phenomenex 5 μm C18 column 4.6×50 mm, 10–90% aqueous methanol over 4 minutes containing 0.2% phosphoric acid, 4 mL/min, monitoring at 220 nm).

B. 1-Amino-3,3-dimethyl-2-butanone hydrochloride

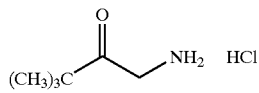

N-(3,3-Dimethyl-2-butanonyl)hexamethylenetetraminium bromide (400 g, 1.254 mol, 1 eq) was combined in 2 L of ethanol with 12 N aqueous HCl (439 mL, 5.26 mol, 4.2 eq). The reaction mixture was stirred at 75° C. for 1 h and then allowed to cool to rt. The resulting slurry was filtered. The filtrate was concentrated in vacuo and isopropyl alcohol was added. The solution was filtered again. Addition of 1.2 L of ether caused the desired material to precipitate from solution. The material was filtered, washed with ether (2×300 mL), and dried in vacuo at 50° C. overnight to provide 184.1 g (97%) of 1-amino-3,3-dimethyl-2-butanone hydrochloride.

C. N-Chloroacetyl-1-amino-3,3-dimethyl-2-butanone

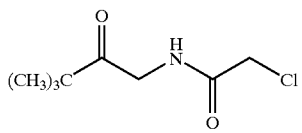

1-Amino-3,3-dimethyl-2-butanone hydrochloride (130.96 g, 0.8637 mol, 1 eq) was dissolved in 3.025 L of $CH_2Cl_2$ under $N_2$ at −5° C. Triethylamine (301 mL, 2.16 mol, 2.5 eq) was added followed by chloroacetyl chloride (75.7 mL, 0.450 mol, 1.1 eq) in 175 mL of $CH_2Cl_2$. The resulting slurry was stirred at −5 to −10° C. for 2 h. Water (1.575 L) was added followed by 175 mL of concentrated HCl. The organic phase was washed a second time with 1.75 L of 10% aqueous HCl, and then with 500 mL of water. The organic phase was dried over $Na_2SO_4$ and concentrated in vacuo to provide 155.26 g (93.8%) of N-chloroacetyl-1-amino-3,3-dimethyl-2-butanone HPLC R.T.=2.27 min (Phenomenex 5 μm C18 column 4.6×50 mm, 10–90% aqueous methanol over 4 minutes containing 0.2% phosphoric acid, 4 mL/min, monitoring at 220 nm).

D. 5-t-Butyl-2-chloromethyloxazole

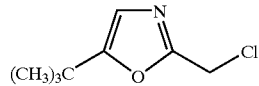

N-Chloroacetyl-1-amino-3,3-dimethyl-2-butanone (180.13 g, 0.9398 mol, 1 eq) was combined with phosphorus oxychloride (262 mL, 2.8109 mol, 3 eq) under $N_2$. The reaction mixture was heated at 105° C. for 1 h. The mixture was cooled to rt and then quenched with 1.3 kg of ice. The aqueous phase was extracted with ethyl acetate (1 L, then 2×500 mL). The organic extracts were washed with saturated aqueous $NaHCO_3$ (4×1 L) which was back-extracted several times with ethyl acetate. The organic phases were combined, washed with saturated aqueous $NaHCO_3$ (500 mL) followed by saturated aqueous NaCl (300 mL), dried over $MgSO_4$, and concentrated in vacuo to give a brown oil. The crude material was distilled under high vacuum at 100° C. to provide 155.92 g (96%) of 5-t-butyl-2-chloromethyloxazole. HPLC R.T.=3.62 min (Phenomenex 5 μm C18 column 4.6×50 mm, 10–90% aqueous methanol over 4 minutes containing 0.2% phosphoric acid, 4 mL/min, monitoring at 220 nm).

Alternate method using Burgess' reagent: As an alternative, 5-t-butyl-2-chloromethyloxazole may be prepared by reaction of a suitable chloroamide with 2 eq of Burgess' salt in tetrahydrofuran.

E. 5-t-Butyl-2-(5-thioureamethyl)oxazole

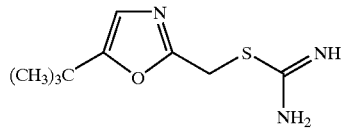

5-t-Butyl-2-chloromethyloxazole (1.77 g, 10.2 mmol, 1.02 eq) was combined with thiourea (0.76 g, 9.98 mmol, 1 eq) under $N_2$ in 10 mL of absolute ethanol. The reaction mixture was heated at reflux for 1.5 h. The mixture was cooled to rt and concentrated in vacuo. Trituration of the resulting crude material with t-butyl methyl ether provided 2.32 g (93%) of 5-t-butyl-2-(5-thioureamethyl)oxazole. HPLC R.T.=2.05 min (Phenomenex 5 μm C18 column 4.6×50 mm, 10–90% aqueous methanol over 4 minutes containing 0.2% phosphoric acid, 4 mL/min, monitoring at 220 nm); $^1$H NMR (d-DMSO): δ9.48 (s, 3H), 6.85 (s, 1H), 4.73 (s, 2H), 1.24 (s, 9H).

F. 2-Amino-5-[[[5-(1,1-dimethylethyl)-2-oxazoly]methyl]thio]-thiazole

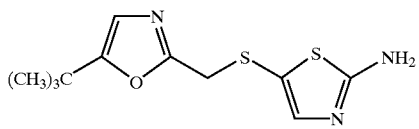

5-t-Butyl-2-(5-thioureamethyl)oxazole (1.25 g, 5 mmol, 1 eq) was added to a mixture of NaOH (3.0 g, 75 mmol, 15 eq), water (10 mL), toluene (10 mL), and tetrabutylammonium sulfate (50 mg, 0.086 mmol, 0.017 eq). 5-Bromo-2-aminothiazole hydrobromide (1.70 g, 5 mmol, 1 eq) was added and the reaction mixture was stirred at rt for 14.5 h. The mixture was diluted with water and extracted twice with ethyl acetate. The organic extracts were washed with water (4×10 mL), dried over MgSO$_4$, and concentrated in vacuo to provide 1.1 g (82%) of 2-amino-5-[[[5-(1,1-dimethylethyl)-2-oxazolyl]methyl]thio]-thiazole. HPLC 86.3% at 2.75 min (Phenomenex 5 μm C18 column 4.6×50 mm, 10–90% aqueous methanol over 4 minutes containing 0.2% phosphoric acid, 4 mL/min, monitoring at 220 nm); $^1$H NMR (CDCl$_3$): δ6.97 (s, 1H), 6.59 (s, 1H), 5.40 (br s, 2H), 3.89 (s, 2H), 1.27 (s,9H).

G. N-[5-[[[5-(1,1-Dimethylethyl)-2-oxazolyl]methyl]thio]-2-thiazolyl]-4-piperidinecarboxamide

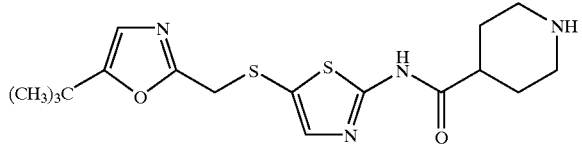

1-(3-Dimethylaminopropyl)-3-ethylcarbodiimide hydrochloride (13.8 g, 72 mmol, 2 eq) was added to a mixture of 2-amino-5-[[[5-(1,1-dimethylethyl)-2-oxazolyl]methyl]thio]-thiazole (9.6 g, 35.6 mmol, 1 eq), N-t-butoxycarbonyl-isonipecotic acid (12.6 g, 55 mmol, 1.5 eq), 4-(dimethylamino)pyridine (2 g, 16 mmol, 0.45 eq), N,N-dimethylformamide (36 mL) and CH$_2$Cl$_2$ (100 mL). The clear reaction mixture became cloudy as it was stirred at rt for 3.5 h. Water (300 mL) and ethyl acetate (200 mL) were added and the resulting precipitate was filtered off. The filtrate was extracted with ethyl acetate. The organic extracts were dried over MgSO$_4$ and concentrated in vacuo to provide a yellow solid which was combined with the precipitate. The solid was boiled in a mixture of ethanol, acetone, and water for 20 min. The solid was filtered, washed with an ethanol/water mixture, and dried to give a BOC-coupled intermediate (16.6 g) as a white solid. A magnetically-stirred suspension of the BOC-coupled intermediate (20.2 g) in 200 mL of chloroform was warmed until homogeneous then a solution of 4N HCl in dioxane (31 mL) was added at 55° C. Gas was evolved and a precipitate formed within a few minutes. After 7 hr, HPLC indicated the reaction was about ⅔ complete. Additional 4N HCl in dioxane (10 mL) was introduced and the reaction mixture was stirred at 60° C. for 1 hr followed by room temperature overnight. A third portion (10 mL) of 4N HCl in dioxane was added and the reaction mixture stirred at 45° C. for 6 hr. The resultant heavy suspension was stirred at room temperature overnight then cooled in an ice-bath and saturated aq sodium bicarbonate solution (200 mL) was added. Gas was evolved during the addition. The heavy suspension became homogeneous then formed a light suspension. The light suspension was treated with 6 g of solid sodium carbonate, heated at 60° C. for 20 minutes, and diluted with chloroform (100 mL). The aqueous phase was separated and extracted with chloroform (2×100 mL). The organics were combined, washed with brine (100 mL), dried (sodium carbonate and sodium sulfate), and concentrated in vacuo to give a yellow solid. The yellow solid was dissolved in warm 95% ethanol (200 mL), diluted with water (200 mL), warmed until homogeneous, and cooled overnight in a refrigerator. The resultant solid was collected, washed with 1:1 ethanol/water, and dried at 50° C. under vacuum overnight to give N-[5-[[[5-(1,1-dimethylethyl)-2-oxazolyl]methyl]thio]-2-thiazolyl]-4-piperidinecarboxamide as a white solid (13.3 g, mp 171–173° C.). LC/MS: 381 [M+H]$^+$; HPLC: HI>99% at 3.12 min (YMC S5 ODS column 4.6×50 mm, 10–90% aqueous methanol over 4 minutes containing 0.2% phosphoric acid, 4 mL/min, monitoring at 220 nm).

EXAMPLE 2

Preparation of (±)-N-[5-[[[5-(1,1-Dimethylethyl)-2-oxazolyl]methyl]thio]-2-thiazolyl]-3-piperidinecarboxamide

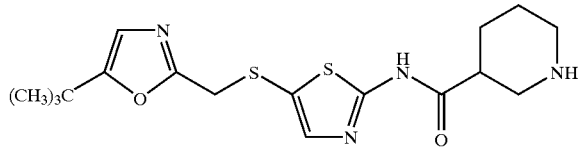

A. (±)-N-t-butoxycarbonyl-nipecotic acid

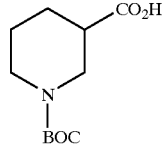

Nipecotic acid (1.3 g, 10 mmol, 1 eq) was combined with 10 mL of dioxane, 2 mL of acetonitrile, 10 mL of water, and 10 mL of 1N aqueous NaOH (1 eq). Di-t-butyl dicarbonate (3.3 g, 15 mmol, 1.5 eq) was added and the reaction mixture was stirred at rt overnight. The reaction mixture was concentrated in vacuo to remove organic solvent and 10% aqueous citric acid was added The mixture was extracted with ethyl acetate (3×100 mL). The organic extracts were dried over Na$_2$SO$_4$, filtered through silica gel, and concentrated in vacuo. The crude material was recrystallized from ethyl acetate and hexanes to provide 2.2 g (96%) of (±)-N-t-butoxycarbonyl-nipecotic acid as a white solid.

B. (±)-N-[5-[[[5-(1,1-Dimethylethyl)-2-oxazoly]methyl]thio]-2-thiazolyl]-(N-t-butoxycarbonyl)-3-piperidinecarboxamide

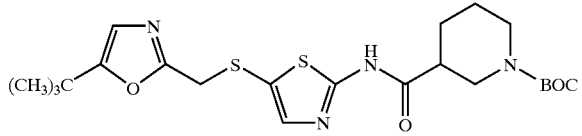

1-(3-Dimethylaminopropyl)-3-ethylcarbodiimide hydrochloride (383 mg, 2 mmol, 2 eq) was added to a mixture of 2-amino-5-[[[5-(1,1-dimethylethyl)-2-oxazolyl]methyl]thio]-thiazole (270 mg, 1 mmol, 1 eq), N-t-butoxycarbonyl-nipecotic acid (344 mg, 1.5 mmol, 1.5 eq), 4-(dimethylamino)pyridine (61 mg, 0.5 mmol, 0.5 eq), N,N-dimethylformamide (1 mL) and CH$_2$Cl$_2$ (6 mL). The reaction mixture was stirred at rt for 1.3 h. Triethylamine (0.28 mL, 2 mmol, 2 eq) was added, and the reaction mixture was stirred for 1 h. Additional N-t-butoxycarbonyl-nipecotic acid (340 mg), triethylamine (0.28 mL) and 1-(3-dimethylaminopropyl)-3-ethylcarbodiimide hydrochloride (380 mg) were added. After 1 h, no further change was observed. Additional 4-(dimethylamino)pyridine, N,N-dimethylformamide, triethylamine and starting acid were added and the reaction was stirred overnight at rt. The resulting black solution was diluted with saturated aqueous NaHCO$_3$ and extracted with CH$_2$Cl$_2$. The organic extracts were dried, concentrated in vacuo, and purified by flash chromatography on silica gel eluting with a gradient of 50–100% ethyl acetate in hexanes to provide 397 mg (83%) of (±)-N-[5-[[[5-(1,1-dimethylethyl)-2-oxazolyl]methyl]thio]-2-thiazolyl]-(N-t-butoxycarbonyl)-3-piperidinecarboxamide as a yellow glassy solid.

C. (±)-N-[5-[[[5-(1,1-Dimethylethyl)-2-oxazolyl]methyl]thio]-2-thiazolyl]-3-piperidinecarboxamide

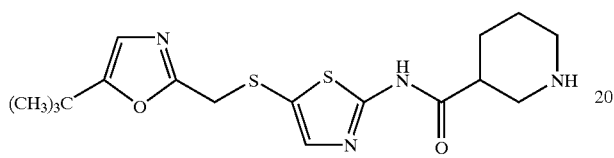

(±)-N-[5-[[[5-(1,1-Dimethylethyl)-2-oxazolyl]methyl]thio]-2-thiazolyl]-(N-t-butoxycarbonyl)-3-piperidinecarboxamide (355 mg, 0.74 mmol, 1 eq) was dissolved in 3 mL of CH$_2$Cl$_2$. Trifluoroacetic acid (3 mL) was added, and the mixture was stirred at rt for 20 min. The reaction mixture was concentrated in vacuo and neutralized with saturated aqueous NaHCO$_3$. The resulting mixture was extracted with ethyl acetate. The organic extracts were dried over Na$_2$SO$_4$, concentrated in vacuo, and recrystallized from ethyl acetate to provide 142 mg (50%) of (±)-N-[5-[[[5-(1,1-dimethylethyl)-2-oxazolyl]methyl]thio]-2-thiazolyl]-3-piperidinecarboxamide as a white solid. MS: 381 [M+H]$^+$; HPLC: 100% at 3.15 min (YMC S5 ODS column 4.6×50 mm, 10–90% aqueous methanol over 4 minutes containing 0.2% phosphoric acid, 4 mL/min, monitoring at 220 nm).

EXAMPLE 3

Preparation of (±)-1-(2,3-Dihydroxypropyl)-N-[5-[[[5-(1,1-dimethylethvl)-2-oxazolyl]methyl]thio]-2-thiazolyl]-4-piperidinecarboxamide

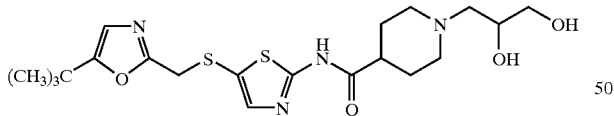

N-[5-[[[5-(1,1-Dimethylethyl)-2-oxazolyl]methyl]thio]-2-thiazolyl]-4-piperidinecarboxamide (66 mg, 0.17 mmol, 1 eq) was combined with glyceraldehyde (69 mg, 0.77 mmol, 4.5 eq), sodium triacetoxyborohydride (163 mg, 0.77 mmol, 4.5 eq) and 1,2-dichloroethane (4 mL). The resulting suspension was stirred at rt for 4 h. Methanol (1 mL) was added and the reaction mixture was stirred at rt overnight, concentrated in vacuo and purified by preparative HPLC to provide 69 mg (59%) of (±)-1-(2,3-dihydroxypropyl)-N-[5-[[[5-(1,1-dimethylethyl)-2-oxazolyl]methyl]thio]-2-thiazolyl]-4-piperidinecarboxamide as a white solid. MS: 455 [M+H]$^+$; HPLC: 100% at 3.06 min (YMC S5 ODS column 4.6×50 mm, 10–90% aqueous methanol over 4 minutes containing 0.2% phosphoric acid, 4 mL/min, monitoring at 220 nm).

EXAMPLE 4

Preparation of N-[5-[[[5-(1,1-Dimethylethyl)-2-oxazoly]methyl]thio]-2-thiazolyl]-1-(1-methylethyl)-4-piperidinecarboxamide

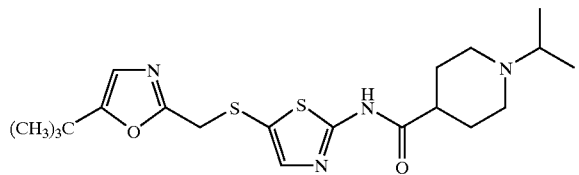

A. Ethyl 1-(1-methylethyl)-4-piperidine carboxylate

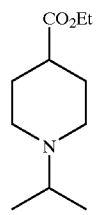

Ethyl isonipecotate (3.2 g, 20 mmol, 1 eq) was combined with acetone (5.8 g, 100 mmol, 5 eq), sodium triacetoxyborohydride (10.5 g, 50 mmol, 2.5 eq) and 1,2-dichloroethane (200 mL). The reaction mixture was stirred at rt for 72 h. Saturated aqueous NaHCO$_3$ was added, and the mixture was extracted with CH$_2$Cl$_2$. The organic extracts were dried, filtered through a silica gel pad, and concentrated in vacuo to provide 3.72 g (93%) of ethyl 1-(1-methylethyl)-4-piperidine carboxylate as a colorless liquid.

B. 1-(1-Methylethyl)-4-piperidine carboxylic acid

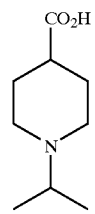

Ethyl 1-(1-methylethyl)-4-piperidine carboxylate (3.6 g, 18 mmol, 1 eq) was combined with barium hydroxide octahydrate (10.4 g, 33 mmol, 1.8 eq) in a mixture of 70 mL of water with 44 mL of ethanol. The mixture was heated at 60° C. for 1.3 h. The reaction mixture was concentrated in vacuo and diluted with 70 mL of water. Ammonium carbonate (6.9 g, 87 mmol, 4.8 eq) was added portionwise and the reaction mixture was stirred at rt overnight. The mixture was filtered through diatomaceous earth, concentrated, and lyophilized to provide 3.1 g (100%) of 1-(1-methylethyl)-4-piperidine carboxylic acid as a white solid.

C. N-[5-[[[5-(1,1-Dimethylethyl)-2-oxazolyl]methyl]thio]-2-thiazolyl]-1-(1-methylethyl)-4-piperidinecarboxamide

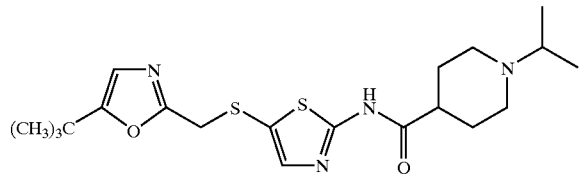

1-(3-Dimethylaminopropyl)-3-ethylcarbodiimide hydrochloride (1.0 g, 5.2 mmol, 2 eq) was added to a mixture of 2-amino-5-[[[5-(1,1-dimethylethyl)-2-oxazolyl]methyl]thio]thiazole (0.7 g, 2.6 mmol, 1 eq), 1-(1-methylethyl)-4-piperidine carboxylic acid (0.78 g, 3.9 mmol, 1.5 eq), 4-(dimethylamino)pyridine (0.16 g, 1.3 mmol, 0.5 eq), N,N-dimethylformamide (2.6 mL) and $CH_2Cl_2$ (7.8 mL). The reaction mixture was stirred at rt for 1 h, diluted with 30 mL of water and extracted with ethyl acetate (2×70 mL). The organic extracts were dried over $Na_2SO_4$, concentrated in vacuo, and purified by flash chromatography on silica gel eluting with a gradient of 5–10% triethylamine in ethyl acetate. The material was recrystallized from ethanol and water to provide 0.93 g (85%) of N-[5-[[[5-(1,1-dimethylethyl)-2-oxazolyl]-methyl]thio]-2-thiazolyl]-1-(1-methylethyl)-4-piperidinecarboxamide as a yellowish solid. MS: 423 [M+H]$^+$; HPLC: 100% at 3.15 min (YMC S5 ODS column 4.6×50 mm, 10–90% aqueous methanol over 4 minutes containing 0.2% phosphoric acid, 4 mL/min, monitoring at 220 nm).

EXAMPLE 5

Preparation of 1-Cyclopropyl-N-[5-[[[5-(1,1-dimethylethyl)-2-oxazolyl]methyl]thio]-2-thiazolyl]-4-piperidinecarboxamide

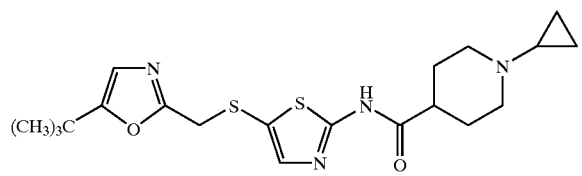

A. 1-Cyclopropyl-4-piperidine carboxylic acid

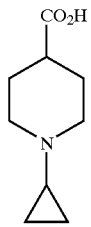

Ethyl isonipecotate (1.57 g, 10 mmol, 1 eq) was combined with ((1-ethoxycyclopropyl)oxy)trimethyl silane (8.7 g, 50 mmol, 5 eq) in 100 mL of methanol. Acetic acid (5.7 mL, 100 mmol, 10 eq) and molecular sieves were added. After 30 min at rt, sodium triacetoxyborohydride (2.5 g, 40 mmol, 4 eq) was added and the reaction mixture was heated at 65° C. overnight. The reaction mixture was cooled and $Na_2CO_3$ (20 g) was added. The mixture was stirred at rt for 2 h and filtered through diatomaceous earth. The diatomaceous earth was washed with methanol. The filtrates were combined, concentrated in vacuo, diluted with water, and extracted with ethyl acetate. The organic extracts were dried, filtered through a silica gel pad, and concentrated in vacuo to provide 2.4 g of colorless liquid. This material was combined with barium hydroxide octahydrate (5.7 g, 18 mmol, 1.8 eq) in a mixture of 38 mL of water with 24 mL of ethanol. The mixture was heated at 60° C. for 1 h. The reaction mixture was concentrated in vacuo and diluted with 38 mL of water. Ammonium carbonate (3.8 g) was added portionwise and the reaction was stirred at rt for 2 h. The mixture was filtered through diatomaceous earth, washing with water. The filtrate was washed with ethyl acetate. Concentration of the aqueous phase provided 1.56 g (92%) of 1-cyclopropyl-4-piperidine carboxylic acid as a hygroscopic white solid.

B. 1-Cyclopropyl-N-[5-[[[5-(1,1-dimethylethyl)-2-oxazolyl]-methyl]-thio]-2-thiazolyl]-4-piperidinecarboxamide

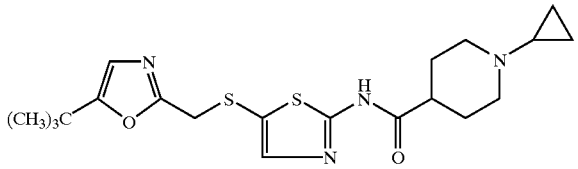

1-(3-Dimethylaminopropyl)-3-ethylcarbodiimide hydrochloride (1.0 g, 5.2 mmol, 2 eq) was added to a mixture of 2-amino-5-[[[5-(1,1-dimethylethyl)-2-oxazolyl]methyl]thio]thiazole (0.7 g, 2.6 mmol, 1 eq), 1-cyclopropyl-4-piperidine carboxylic acid (0.77 g, 3.9 mmol, 1.5 eq), 4-(dimethylamino)pyridine (0.16 g, 1.3 mmol, 0.5 eq), N,N-dimethylformamide (2.6 mL) and $CH_2Cl_2$ (7.8 mL). The reaction mixture was stirred at rt for 1 h, diluted with water (30 mL), and extracted with ethyl acetate (2×70 mL). The combined organic extracts were dried over anhydrous sodium sulfate, concentrated in vacuo, and purified by flash chromatography on silica gel eluting with a gradient of 0–10% triethylamine in ethyl acetate. The material was crystallized from ethyl acetate and hexanes to provide 0.7 g (65%) of 1-cyclopropyl-N-[5-[[[5-(1,1-dimethylethyl)-2-oxazolyl]methyl]thio]-2-thiazolyl]-4-piperidinecarboxamide as white crystals. MS: 421 [M+H]$^+$; HPLC: 100% at 3.13 min (YMC S5 ODS column 4.6×50 mm, 10–90% aqueous methanol over 4 minutes containing 0.2% phosphoric acid, 4 mL/min, monitoring at 220 nm).

EXAMPLE 6

Preparation of N-[5-[[[5-(1,1-Dimethylethyl)-2-oxazolyl]methyl]thio]-2-thiazolyl]-1-(2-hydroxyethyl)-4-piperidinecarboxamide

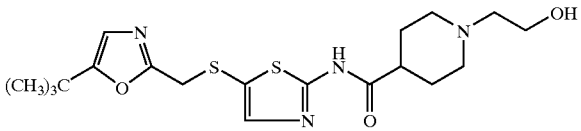

A. N-[5-[[[5-(1,1-Dimethylethyl)-2-oxazolyl]methyl]thio]-2-thiazolyl]1-(2-dimethyl-t-butylsilyloxyethyl)-4-piperidinecarboxamide

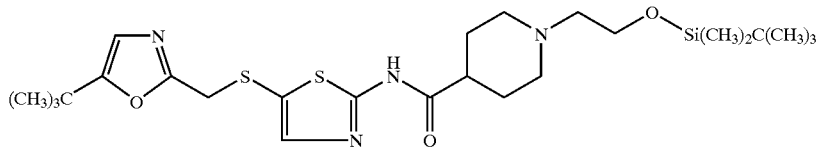

N-[5-[[[5-(1,1-dimethylethyl)-2-oxazolyl]methyl]thio]-2-thiazolyl]-4-piperidinecarboxamide (1.4 g, 3.68 mmol, 1 eq) was dissolved in 30 mL of N,N-dimethylformamide and 100 mL of tetrahydrofuran. 2-(Bromoethoxy)-t-butyldimethylsilane (0.79 mL, 3.68 mmol, 1 eq), and NaHCO$_3$ were added and the reaction mixture was stirred at 50° C. for 23 h. Additional 2-(bromoethoxy)-t-butyldimethylsilane (0.9 mL) was added, and the reaction mixture was stirred at 50° C. for 22 h, cooled, concentrated in vacuo and diluted with water (25 mL). The resultant aqueous mixture was extracted with ethyl acetate (50 mL). The organic extract was dried over Na$_2$SO$_4$, concentrated in vacuo, and purified by flash chromatography on silica gel eluting with a gradient of 0–5% triethylamine in ethyl acetate to provide 1.7g (84%) of N-[5-[[[5-(1,1-dimethylethyl)-2-oxazolyl]methyl]thio]-2-thiazolyl]-1-(2-dimethyl-t-butylsilyloxyethyl)-4-piperidinecarboxamide as a yellow solid. MS: 539 [M+H]$^+$; HPLC: 98% at 4.01 min (YMC S5 ODS column 4.6×50 mm, 10–90% aqueous methanol over 4 minutes containing 0.2% phosphoric acid, 4 mL/min, monitoring at 220 nm).

B. N-5-[[[5-(1,1-Dimethylethyl)-2-oxazolyl]methyl]thio]-2-thiazolyl]-1-(2-hydroxyethyl)-4-piperidinecarboxamide

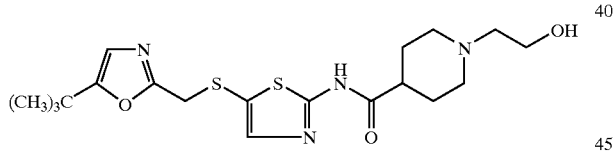

N-[5-[[[5-(1,1-Dimethylethyl)-2-oxazolyl]methyl]thio]-2-thiazolyl]-1-(2-dimethyl-t-butylsilyloxyethyl)-4-piperidinecarboxamide (1.45 g, 2.7 mmol, 1 eq) was dissolved in 100 mL of acetonitrile and combined with aqueous HF (48% aqueous, 2.5 mL). The reaction mixture was stirred for 4 h at rt. An additional 2.5 mL of aqueous HF was added, and the reaction mixture was stirred overnight. Ethyl acetate (100 mL) and saturated aqueous NaHCO$_3$ (50 mL) were added. Additional solid NaHCO$_3$ was added to make the mixture basic. The mixture was extracted with ethyl acetate (2×50 mL). The organic extracts were dried over Na$_2$SO$_4$, filtered through a pad of silica gel, and concentrated in vacuo. The resulting white solid was crystallized from ethanol and water to provide 1.6 g (59%) of N-[5-[[[5-(1,1-dimethylethyl)-2-oxazolyl]methyl]thio]-2-thiazolyl]-1-(2-hydroxyethyl)-4-piperidinecarboxamide as a white solid. MS: 425 [M+H]$^+$; HPLC: 100% at 3.05 min (YMC S5 ODS column 4.6×50 mm, 10–90% aqueous methanol over 4 minutes containing 0.2% phosphoric acid, 4 mL/min, monitoring at 220 nm).

EXAMPLE 7

Preparation of (R)-N-[5-[[[5-(1,1-Dimethylethyl)-2-oxazolyl]methyl]thio]-2-thiazolyl]-3-piperidinecarboxamide hydrochloride

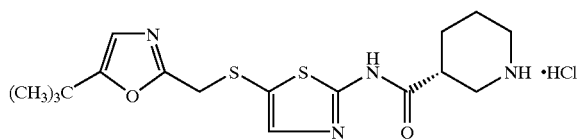

A. (R)- and (S)-N-[5-[[[5-(1,1-Dimethylethyl)-2-oxazolyl]methyl]thio]-2-thiazolyl-(N-t-butoxycarbonyl)-3-piperidinecarboxamide (R)

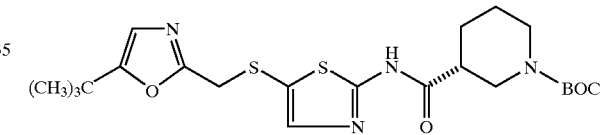

(S)

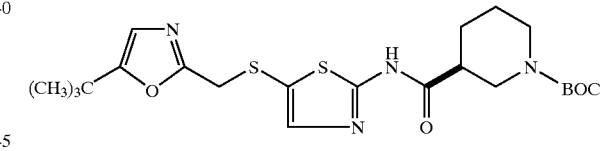

1-(3-Dimethylaminopropyl)-3-ethylcarbodiimide hydrochloride (3.8 g, 20 mmol, 2 eq) was added to a mixture of 2-amino-5-[[[5-(1,1-dimethylethyl)-2-oxazolyl]methyl]thio]thiazole (2.7 g, 10 mmol, 1 eq), N-t-butoxycarbonyl-nipecotic acid (3.4 g, 1.5 mmol, 1.5 eq), N,N-dimethylformamide (10 mL) and CH$_2$Cl$_2$ (30 mL). The reaction mixture was stirred at rt for 4 h. The resulting black solution was concentrated in vacuo, diluted with water (90 mL) and extracted with ethyl acetate (100 mL, then 2×75 mL). The organic extracts were dried over Na$_2$CO$_3$, concentrated in vacuo, and purified by flash chromatography on silica gel eluting with a gradient of 50–100% ethyl acetate in hexanes to provide 3.8 g (79%) of a yellow solid. The enantiomers were separated by chiral HPLC (Chiral Pak AD 5×50 cm 20µ: eluent 10% (0.1% triethylamine in isopropanol) in hexanes; 45 mL/min, detection at 254 nm, loading 300 mg in 5 mL of isopropanol) to give each of the two optically pure isomers: 1.65 g of the R isomer and 1.65 g of the S isomer.

B. (R)-N-[5-[[[5-(1,1-Dimethylethyl)-2-oxazolyl]methyl]thio]-2-thiazolyl]-3-piperidinecarboxamide hydrochloride

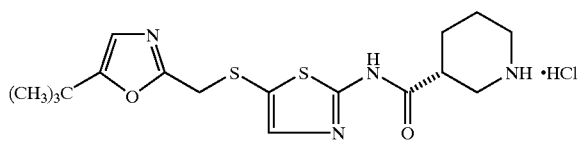

The (R) isomer of Part A (1.65 g, 3.43 mmol, 1 eq) was dissolved in 10 mL of $CH_2Cl_2$. Trifluoroacetic acid (6 mL) was added, and the mixture was stirred at rt for several hours. The reaction mixture was concentrated in vacuo and neutralized with saturated aqueous $NaHCO_3$. The resulting mixture was stirred with ethyl acetate for 1 h. The organic extracts were dried over $Na_2SO_4$ and concentrated in vacuo to provide a yellowish solid. The solid was dissolved in methanol and 1 eq of 1N aqueous HCl was added. The resulting solution was lyophilized to provide 1 g (77%) of (R)-N-[5-[[[5-(1,1-dimethylethyl)-2-oxazolyl]methyl]thio]-2-thiazolyl]-3-piperidinecarboxamide hydrochloride as a yellow solid. MS: 381 [M+H]$^+$; HPLC: 100% at 3.14 min (YMC S5 ODS column 4.6×50 mm, 10–90% aqueous methanol over 4 minutes containing 0.2% phosphoric acid, 4 mL/min, monitoring at 220 nm).

EXAMPLE 8

Preparation of (S)-N-[5-[[[5-(1,1-Dimethylethyl)-2-oxazolyl]methyl]thio]-2-thiazolyl]-3-piperidinecarboxamide hydrochloride

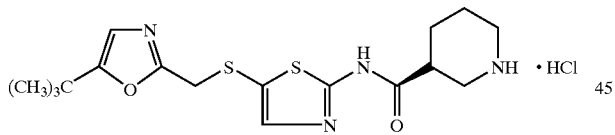

The (S) isomer of Example 7, Part A (1.65 g, 3.43 mmol, 1 eq) was dissolved in 10 mL of $CH_2Cl_2$. Trifluoroacetic acid (6 mL) was added, and the mixture was stirred at rt for several hours. The reaction was concentrated in vacuo and neutralized with saturated aqueous $NaHCO_3$. The resulting mixture was stirred with ethyl acetate for 1 h. The organic extracts were dried over $Na_2SO_4$ and concentrated in vacuo to provide a yellowish solid. The solid was dissolved in methanol and 1 eq of 1N aqueous HCl was added. The resulting solution was lyophilized to provide 0.918 g (70%) of (S)-N-[5-[[[5-(1,1-dimethylethyl)-2-oxazolyl]methyl]thio]-2-thiazolyl]-3-piperidinecarboxamide hydrochloride as a yellow solid. MS: 381 [M+H]$^+$; HPLC: 100% at 3.15 min (YMC S5 ODS column 4.6×50 mm, 10–90% aqueous methanol over 4 minutes containing 0.2% phosphoric acid, 4 mL/min, monitoring at 220 nm).

EXAMPLE 9

Preparation of cis-4-Amino-N-[5-[[[5-(1,1-dimethylethyl)-2-oxazolyl]methyl]thio]-2-thiazolyl] cyclohexylcarboxamide hydrochloride and trans-4-Amino-N-[5-[[[5-(1,1-dimethylethyl)-2-oxazolyl]methyl]thio]-2-thiazolyl]-cyclohexylcarboxamide hydrochloride

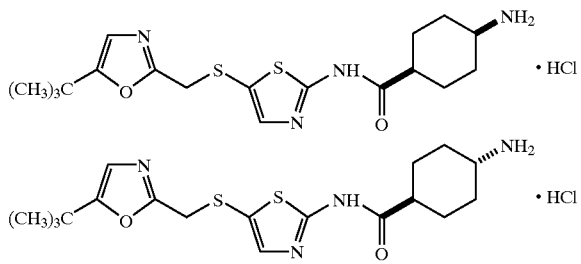

A. 4-(t-Butoxycarbonylamino)cyclohexane carboxylic acid

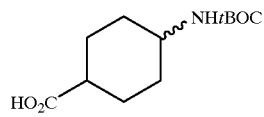

To a solution of 2.86 g (20 mmol) of 4-aminocyclohexane carboxylic acid in 40 mL of 0.5M aqueous NaOH solution, 20 mL of dioxane and 4 mL of acetonitrile was added a total of 6.5 g (30 mmol) of tBoc anhydride at room temperature. After 20 h, 100 mL of ethyl acetate and 100 mL of 10% aqueous citric acid solution were introduced. The aqueous layer which formed was separated and extracted with three-50 mL portions of ethyl acetate. The organic phases were combined, dried (sodium sulfate) and concentrated in vacuo to give 6.0 g (125%) of crude 4-(t-butoxycarbonylamino) cyclohexane carboxylic acid as a colorless oil which solidified upon standing.

B. 4-(t-Butoxycarbonylamino)-N-[5-[[[5-(1,1-dimethylethyl)-2-oxazolyl]-methyl]thio]-2-thiazolyl] cyclohexylcarboxamide

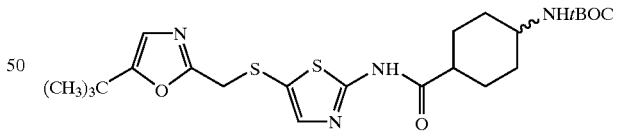

To a solution of 5 g of crude 4-(t-butoxycarbonylamino) cyclohexane carboxylic acid and 3.50 g (13 mmol) of 2-amino-5-[[[5-(1,1-dimethylethyl)-2-oxazolyl]methyl] thio]thiazole in 13 mL of N,N-dimethylformamide and 36 mL of methylene chloride was added 5.0 g (26 mmol) of 1-(3-dimethylaminopropyl)-3-ethylcarbodiimide hydrochloride at room temperature. The reaction mixture was stirred overnight and diluted with 100 mL of water. The aqueous layer was separated and extracted with two-150 mL portions of ethyl acetate. The combined organic phases were dried (sodium sulfate) then filtered through a pad of silica gel. The filtrate was concentrated in vacuo to afford an orange solid. The crude material was recrystallized (95% ethanol) to give 4-(t-butoxycarbonylamino)-N-[5-[[[5-(1,1-dimethylethyl)-2-oxazolyl]methyl]thio]-2-thiazolyl]cyclohexylcarboxamide as a yellow solid. The mother liquors were also concentrated in vacuo to give additional 4-(t-butoxycarbonylamino)-N-[5-[[[5-(1,1-dimethylethyl)-2-oxazolyl]methyl]thio]-2-thiazolyl]cyclohexylcarboxamide as a brown solid.

C. cis-4-Amino-N-[5-[[[5-(1,1-dimethylethyl)-2-oxazolyl]methyl]thio]-2-thiazolyl]cyclohexylcarboxamide hydrochloride and trans-4-Amino-N-[5-[[[5-(1,1-dimethylethyl)-2-oxazolyl]methyl]thio]-2-thiazolyl]-cyclohexylcarboxamide hydrochloride

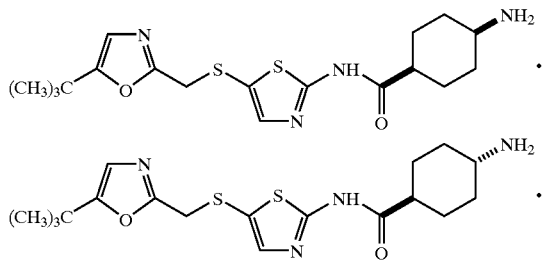

To a suspension of 4-(t-butoxycarbonylamino)-N-[5-[[[5-(1,1-dimethylethyl)-2-oxazolyl]methyl]thio]-2-thiazolyl]cyclohexylcarboxamide (from Part B mother liquors) suspended in 15 mL of methylene chloride was added 5 mL of trifluoroacetic acid at room temperature. The reaction mixture was stirred for 2 h then concentrated in vacuo to remove volatiles. The residue was diluted with water, basified with aqueous NaOH solution then the resulting aqueous solution was extracted with ethyl acetate. The combined organic extracts were dried (sodium sulfate) to give a crude cis/trans product. The crude material was purified by flash chromatography (Merck silica, 25×3 cm, 1:9 isopropylamine/ethyl acetate then 1:2:7 methanol/iso-propylamine/ethyl acetate) to afford 0.74 g of the cis isomer as a yellow solid and 0.50 g of the trans isomer as a brown solid. The cis isomer was dissolved in methanol then 0.34 mL of 5N aqueous HCl was added. The solution was concentrated in vacuo, washed with ether, diluted with water and lyophilized to afford 0.80 g of cis-4-amino-N-[5-[[[5-(1,1-dimethylethyl)-2-oxazolyl]methyl]thio]-2-thiazolyl]cyclohexylcarboxamide hydrochloride as a yellow solid. MS: 395 [M+H]$^+$; HPLC-HI 98% at 3.17 min (YMC S5 ODS column 4.6×50 mm, 10–90% aqueous methanol over 4 minutes containing 0.2% phosphoric acid, 4 mL/min, monitoring at 220 nm). The trans isomer was dissolved in methanol then 0.24 mL of 5N aqueous HCl was added. The solution was concentrated in vacuo, washed with ether, diluted with water and lyophilized to afford 0.54 g of trans-4-amino-N-[5-[[[5-(1,1-dimethylethyl)-2-oxazolyl]methyl]thio]-2-thiazolyl]cyclohexylcarboxamide hydrochloride as an orange solid. MS: 395 [M+H]$^+$; HPLC-HI 96% at 3.22 min (YMC S5 ODS column 4.6×50 mm, 10–90% aqueous methanol over 4 minutes containing 0.2% phosphoric acid, 4 mL/min, monitoring at 220 nm).

EXAMPLE 10

N-[5-[[[5-(1,1-Dimethylethyl)-2-oxazolyl]methyl]thio]-2-thiazolyl]-4-piperidinecarboxamide, monohydrochloride

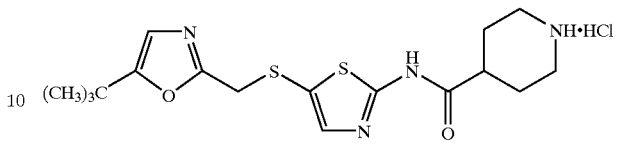

To a solution of 40 mL of absolute EtOH cooled in an ice-bath was added acetyl chloride (0.28 mL, 3.9 mmol) dropwise. The reaction mixture was allowed to warm to room temperature over 30 min then N-[5-[[[5-(1,1-dimethylethyl)-2-oxazolyl]methyl]-thio]-2-thiazolyl]-4-piperidinecarboxamide (1.50 g, 3.94 mmol, 1 eq) was introduced in one portion with stirring to give a thick slurry. Water (~4 mL) was added until homogeneous then concentrated in vacuo to give a crude pale yellow solid. The crude material was recrystallized (aq EtOH) to afford the title compound (70%) as a white solid, mp 256–258°. Analysis calc'd for C17H24N4O2S2.HCl: C, 48.96; H, 6.04; N, 13.43; S, 15.38; Cl, 8.50. Found: C, 48.69; H, 5.99; N, 13.24; S, 15.27; Cl, 8.31.

EXAMPLE 11

N-[5-[[[5-(1,1-Dimethylethyl)-2-oxazolyl]methyl]thio]-2-thiazolyl]-4-piperidinecarboxamide, monohydrobromide

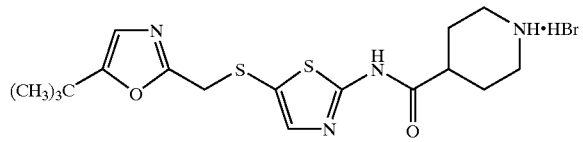

To a solution of 1M HBr in EtOH (0.5 mL) was added N-[5-[[[5-(1,1-dimethylethyl)-2-oxazolyl]methyl]thio]-2-thiazolyl]-4-piperidinecarboxamide (190 mg, 0.5 mmol, 1 eq) then cooled to -40° C. overnight. The solid precipitate that formed was collected on a Buchner funnel, washed with absolute EtOH then dried under vacuum at 100° C. to afford the title compound (72%) as a fine white powder, mp 235–237° C. Analysis calc'd for C17H24N4O2S2.HBr: C, 44.24; H, 5.46; N, 12.14; S, 13.89; Br, 17.31. Found: C, 44.16; H, 5.40; N, 12.12; S, 13.91; Br, 17.70.

EXAMPLE 12

N-15-[[5-(1,1-Dimethylethyl)-2-oxazolyl]methyl]thio]-2-thiazolyl -4-piperidinecarboxamide, 0.5-L-tartaric acid salt

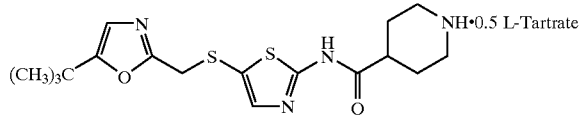

To a warm solution of N-[5-[[[5-(1,1-dimethylethyl)-2-oxazolyl]methyl]thio]-2-thiazolyl]-4-piperidinecarboxamide (1.75 g, 4.6 mmol) in absolute EtOH (70 mL) was added a solution of L-tartaric acid (345 mg, 2.3 mmol, 0.5 eq) in absolute EtOH (5 mL). A precipitate started to form after several minutes. The mixture was allowed to stand for 4 hr at room temperature then the solid precipitate was collected on a Buchner funnel, washed with absolute EtOH and dried under vacuum at 85° C. for 24 hr to afford the title compound (94%) as pale yellow crystals, mp 234–236° C. Analysis calc'd for C17H24N4O2S2.0.5-L-Tartaric acid: C, 50.09; H, 5.97; N, 12.29; S, 14.07. Found: C, 49.85; H, 5.90; N, 12.12; S, 13.75.

EXAMPLE 13

N-[5-[[[5-(1,1-Dimethylethyl)-2-oxazolyl]methyl]thio]-2-thiazolyl] -4-piperidinecarboxamide, 0.5-D-tartaric acid salt

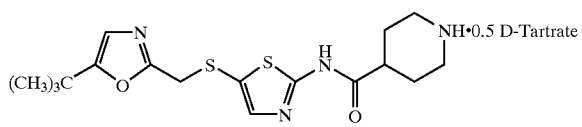

To a warm solution of N-[5-[[[5-(1,1-dimethylethyl)-2-oxazolyl]methyl]thio]-2-thiazolyl]-4-piperidinecarboxamide (1.00 g, 2.63 mmol) in absolute EtOH (40 mL) was added a solution of D-tartaric acid (198 mg, 1.32 mmol, 0.5 eq) in absolute EtOH (4 mL). A precipitate started to form after several minutes. The mixture was allowed to stand for 18 hr at room temperature then the solid precipitate was collected on a Buchner funnel, washed with absolute EtOH and dried under vacuum at 65° C. for 6 hr to afford the title compound (73%) as a white solid, mp 232–233° C. Analysis calc'd for C17H24N4O2S2.0.5-D-Tartaric acid: C, 50.09; H, 5.97; N, 12.29; S, 14.07. Found: C, 49.75; H, 5.81; N, 12.04; S, 13.37.

EXAMPLE 14

N-[5-[[[5-(1,1-Dimethylethyl)-2-oxazolyl]methyl]thio]-2-thiazolyl]-4-piperidinecarboxamide, 0.5-fumaric acid salt

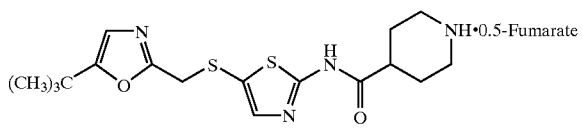

To a warm solution of N-[5-[[[5-(1,1-dimethylethyl)-2-oxazolyl]methyl]thio]-2-thiazolyl]-4-piperidinecarboxamide (1.75 g, 4.6 mmol) in absolute EtOH (100 mL) was added a solution of fumaric acid (276 mg, 2.3 mmol, 0.5 eq) in absolute EtOH (5 mL). A precipitate started to form after 10 minutes. The mixture was allowed to stand for 2 hr at room temperature then at 5° C. for 16 hr. The solid precipitate which formed was collected on a Buchner funnel, washed with absolute EtOH and dried under vacuum at 65° C. for 24 hr to afford the title compound (84%) as a white solid, mp 206–207° C. Analysis calc'd for C17H24N4O2S2.0.5-Fumaric acid: C, 52.04; H, 5.98; N, 12.77; S, 14.62. Found: C, 51.74; H, 5.76; N, 12.57; S, 14.19. Recrystallization (95% aq EtOH) afforded the title compound containing 1 mol EtOH (83%) as large colorless crystals, mp 212–214° C. Analysis calc'd for C17H24N4O2S2.0.5-Fumaric acid.EtOH: C, 52.05; H, 6.66; N, 11.56; S, 13.23. Found: C, 52.03; H, 6.06; N, 11.50; S, 12.99.

EXAMPLE 15

N-[5-[[[5-(1,1-Dimethylethyl)-2-oxazolyl]methyl]thio]-2-thiazolyl]-4-piperidinecarboxamide, 0.5-succinic acid salt

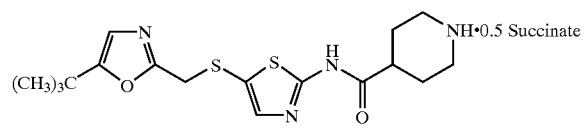

To a warm solution of N-[5-[[[5-(1,1-dimethylethyl)-2-oxazolyl]methyl]thio]-2-thiazolyl]-4-piperidinecarboxamide (50 mg, 0.13 mmol) in absolute EtOH (2 mL) was added a solution of succinic acid (7.7 mg, 0.065 mmol, 0.5 eq) in absolute EtOH (0.25 mL). A precipitate started to form after 10 minutes. The mixture was allowed to stand for 1 hr at room temperature then the precipitate was collected on a Buchner funnel, washed with absolute EtOH and dried under vacuum at 100° C. for 24 hr to afford the title compound (70%) as a white solid, mp 190–192° C. Analysis calc'd for C17H24N4O2S2.0.5-Succinic acid.0.46H2O: C, 50.96; H, 6.28; N, 12.51; S, 14.32. Found: C, 50.96; H, 6.20; N, 12.49; S, 14.23.

EXAMPLE 16

N-5-[[[5-(1,1-Dimethylethyl)-2-oxazolyl]methyl]thio]-2-thiazolyl]-4-piperidinecarboxamide, 0.5-sulfuric acid salt

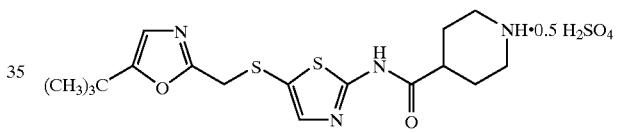

To a warm solution of N-[5-[[[5-(1,1-dimethylethyl)-2-oxazolyl]methyl]thio]-2-thiazolyl]-4-piperidinecarboxamide (50 mg, 0.13 mmol) in absolute EtOH (2 mL) was added a 1M aq solution of sulfuric acid (0.065 mL, 0.065 mmol, 0.5 eq ). A precipitate formed almost immediately. The mixture was cooled to 5° C. for 2 hr then the precipitate was collected on a Buchner funnel, washed with absolute EtOH and dried under vacuum at 100° C. for 24 hr to afford the title compound (79%) as a white solid, mp 256–258° C. Analysis calc'd for C17H24N4O2S2.0.5H2SO4.0.68H2O: C, 46.22; H, 6.01; N, 12.68; S, 18.14. Found: C, 46.21; H, 5.95; N, 12.71; S, 18.23.

EXAMPLE 17

N-[5-[[[5-(1,1-Dimethylethyl)-2-oxazolyl]methyl]thio]-2-thiazolyl]-4-piperidinecarboxamide, 0.5-citric acid salt

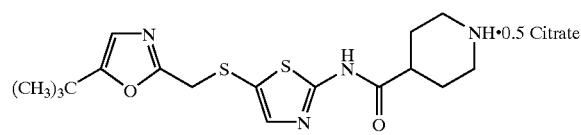

To a warm solution of N-[5-[[[5-(1,1-dimethylethyl)-2-oxazolyl]methyl]thio]-2-thiazolyl]-4- piperidinecarboxamide (50 mg, 0.13 mmol) in absolute EtOH (2 mL) was added a solution of citric acid (8.3 mg, 0.043 mmol, 0.33 eq). The solution was cooled to 5° C. for 18 hr then the precipitate which formed was collected on a Buchner funnel, washed with absolute EtOH and dried under vacuum at 100° C. for 24 hr to afford the title compound (68%) as a white solid, mp 214–216° C. Analysis cal'cd for C17H24N4O2S2.0.5-Citric acid.0.10H2O: C, 50.21; H, 5.94; N, 11.71; S, 13.40. Found: C, 50.21; H, 6.01; N, 11.83; S, 13.44.

EXAMPLE 18

N-[5-[[[5-(1,1-Dimethylethyl)-2-oxazolyl]methyl]thio]-2-thiazolyl]-4-piperidinecarboxamide, methanesulfonic acid salt

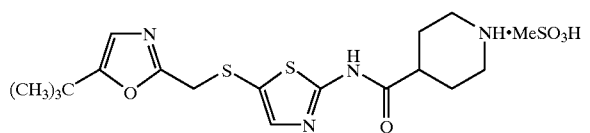

To a slurry of N-[5-[[[5-(1,1-dimethylethyl)-2-oxazolyl]methyl]thio]-2-thiazolyl]-4-piperidinecarboxamide (100 mg, 0.26 mmol) in isopropyl alcohol (0.75 mL) was added methanesulfonic acid (0.017 mL, 0.26 mmol, 1 eq). The slurry was heated to 70° C. to give a clear solution then methyl t-butyl ether (1.5 mL) was added. Within 15 minutes a precipitate formed. The resulting mixture was stirred at 55° C. for 2 hr then at room temperature for 14 hr. The precipitate which formed was collected by filtration then dried under vacuum at 50° C. for 14 hr to afford the title compound (85%) as a colorless powder, mp 105° C. Analysis calc'd for C17H24N4O2S2.MSA.H2O: C, 43.70; H, 6.11; N, 11.32; S, 19.44. Found: C, 43.53; H, 6.14; N, 11.15; S, 19.15.

EXAMPLE 19

N-[5-[[[5-(1,1-Dimethylethyl)-2-oxazolyl]methyl]thio]-2-thiazolyl]-4-piperidinecarboxamide, 0.5-D,L-malic acid salt

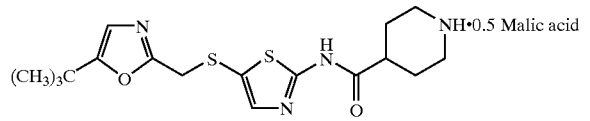

To a solution of N-[5-[[[5-(1,1-dimethylethyl)-2-oxazolyl]methyl]thio]-2-thiazolyl]-4-piperidinecarboxamide (100 mg, 0.26 mmol) in isopropyl alcohol (0.80 mL) was added slowly at 70° C. a solution of D,L-malic acid (35 mg, 0.13 mmol, 0.5 eq ) in isopropyl alcohol (0.3 mL). A precipitate formed immediately. The resulting mixture was stirred at 55° C. for 2 hr then at room temperature for 14 hr. The precipitate was collected by filtration then dried under vacuum at 50° C for 14 hr to afford the title compound (75%) as a colorless powder, mp 216° C. Analysis calc'd for C17H24N4O2S2.0.5-C4H6O5.H2O: C, 50.98; H, 6.08; N, 12.51; S, 14.32. Found: C, 50.55; H, 6.17; N, 12.29; S, 14.05.

What is claimed is:

1. A compound of formula I

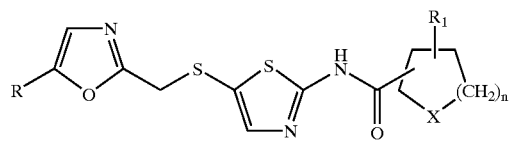

and enantiomers, diastereomers and pharmaceutically acceptable salts thereof wherein R is alkyl;
$R_1$ is hydrogen or alkyl;
X is $NR_2$ or $CHNR_2R_3$;
$R_2$ and $R_3$ are each independently hydrogen, alkyl, substituted alkyl, cycloalkyl or substituted cycloalkyl; and
n is 0, 1, 2 or 3.

2. The compound according to claim 1 wherein

R is alkyl;
$R_1$ is hydrogen;
X is $NR_2$ or $CHNR_2R_3$;
$R_2$ and $R_3$ are each independently hydrogen, alkyl, substituted alkyl or cycloalkyl; and
n is 2.

3. The compound according to claim 1 of formula Ia

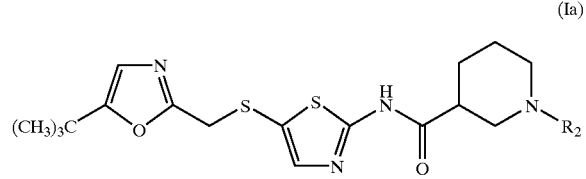

and enantiomers, diastereomers and pharmaceutically acceptable salts thereof wherein $R_2$ is hydrogen, alkyl, substituted alkyl or cycloalkyl.

4. The compound according to claim 1 of formula Ib

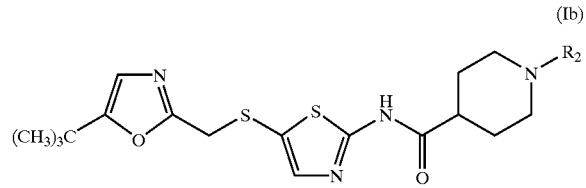

and enantiomers, diastereomers and pharmaceutically acceptable salts thereof wherein $R_2$ is hydrogen, alkyl, substituted alkyl or cycloalkyl.

5. The compound according to claim 1 of formula Ic

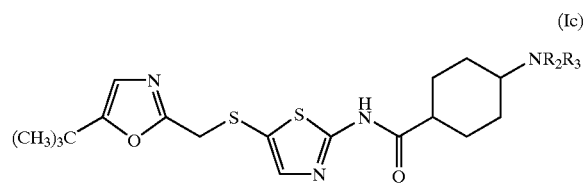

and enantiomers, diasteromers and pharmaceutically acceptable salts thereof wherein $R_2$ and $R_3$ are each independently hydrogen, alkyl, substituted alkyl or cycloalkyl.

6. The compound according to claim 1 selected from the group consisting of

N-[5-[[[5-(1,1-dimethylethyl)-2-oxazolyl]methyl]thio]-2-thiazolyl]-4-piperidinecarboxamide;
(±)-N-[5-[[[5-(1,1-dimethylethyl)-2-oxazolyl]methyl]thio]-2-thiazolyl]-3-piperidinecarboxamide;
(±)-1-(2,3-dihydroxypropyl)-N-[5-[[[5-(1,1-dimethylethyl)-2-oxazolyl]methyl]thio]-2-thiazolyl]-4-piperidinecarboxamide;
N-[5-[[[5-(1,1-dimethylethyl)-2-oxazolyl]methyl]thio]-2-thiazolyl]-1-(1-methylethyl)-4-piperidinecarboxamide;
1-cyclopropyl-N-[5-[[[5-(1,1-dimethylethyl)-2-oxazolyl]methyl]thio]-2-thiazolyl]-4-piperidinecarboxamide;
N-[5-[[[5-(1,1-dimethylethyl)-2-oxazolyl]methyl]thio]-2-thiazolyl]-1-(2-hydroxyethyl)-4-piperidinecarboxamide;
(R)-N-[5-[[[5-(1,1-dimethylethyl)-2-oxazolyl]methyl]thio]-2-thiazolyl]-3-piperidinecarboxamide;
(S)-N-[5-[[[5-(1,1-dimethylethyl)-2-oxazolyl]methyl]thio]-2-thiazolyl]-3-piperidinecarboxamide;
cis-4-amino-N-[5-[[[5-(1,1-dimethylethyl)-2-oxazolyl]methyl]thio]-2-thiazolyl]cyclohexylcarboxamide; and
trans-4-amino-N-[5-[[[5-(1,1-dimethylethyl)-2-oxazolyl]methyl]thio]-2-thiazolyl]cyclohexylcarboxamide; and pharmaceutically acceptable salts thereof.

7. N-[5-[[[5-(1,1-dimethylethyl)-2-oxazolyl]methyl]thio]-2-thiazolyl]-4-piperidinecarboxamide and pharmaceutically acceptable salts thereof.

8. (±)-N-[5-[[[5-(1,1-dimethylethyl)-2-oxazolyl]methyl]thio]-2-thiazolyl]-3-piperidinecarboxamide and pharmaceutically acceptable salts thereof.

9. (R)-N-[5-[[[5-(1,1-dimethylethyl)-2-oxazolyl]methyl]thio]-2-thiazolyl]-3-piperidinecarboxamide and pharmaceutically acceptable salts thereof.

10. (S)-N-[5-[[[5-(1,1-dimethylethyl)-2-oxazolyl]methyl]thio]-2-thiazolyl]-3-piperidinecarboxamide and pharmaceutically salts thereof.

11. cis-4-amino-N-[5-[[[5-(1,1-dimethylethyl)-2-oxazolyl]methyl]thio]-2-thiazolyl]cyclohexylcarboxamide and pharmaceutically acceptable salts thereof.

12. trans-4-amino-N-[5-[[[5-(1,1-dimethylethyl)-2-oxazolyl]methyl]thio]-2-thiazolyl]cyclohexylcarboxamide and pharmaceutically acceptable salts thereof.

13. A pharmaceutical composition which comprises a compound of claim 1 and a pharmaceutically acceptable carrier.

14. A pharmaceutical composition which comprises a compound of claim 1 in combination with a pharmaceutically acceptable carrier and an anti-cancer agent formulated as a fixed dose.

15. A pharmaceutical composition which comprises a compound of claim 1 in combination with a pharmaceutically acceptable carrier and a modulator of p53 transactivation formulated as a fixed dose.

16. A method for modulating apoptosis which comprises administering to a mammalian specie in need thereof an effective apoptosis modulating amount of a compound of claim 1.

17. A method for inhibiting protein kinases which comprises administering to a mammalian specie in need thereof an effective protein kinase inhibiting amount of a compound of claim 1.

18. A method for inhibiting cyclin dependent kinases which comprises administering to a mammalian specie in need thereof an effective cyclin dependent kinase inhibiting amount of a compound of claim 1.

19. A method for inhibiting cdc2 (cdk1) which comprises administering to a mammalian specie in need thereof an effective cdc2 inhibiting amount of a compound of claim 1.

20. A method for inhibiting cdk2 which comprises administering to a mammalian specie in need thereof an effective cdk2 inhibiting amount of a compound of claim 1.

21. A method for inhibiting cdk3 which comprises administering to a mammalian specie in need thereof an effective cdk3 inhibiting amount of a compound of claim 1.

22. A method for inhibiting cdk4 which comprises administering to a mammalian specie in need thereof an effective cdk4 inhibiting amount of a compound of claim 1.

23. A method for inhibiting cdk5 which comprises administering to a mammalian specie in need thereof an effective cdk5 inhibiting amount of a compound of claim 1.

24. A method for inhibiting cdk6 which comprises administering to a mammalian specie in need thereof an effective cdk6 inhibiting amount of a compound of claim 1.

25. A method for inhibiting cdk7 which comprises administering to a mammalian specie in need thereof an effective cdk7 inhibiting amount of a compound of claim 1.

26. A method for inhibiting cdk8 which comprises administering to a mammalian specie in need thereof an effective cdk8 inhibiting amount of a compound of claim 1.

27. A method for treating proliferative diseases which comprises administering to a mammalian specie in need thereof a therapeutically effective amount of a composition of claim 13.

28. A method for treating cancer which comprises administering to a mammalian specie in need thereof a therapeutically effective amount of a composition of claim 13.

29. A method for treating inflammation, inflammatory bowel disease or transplantation rejection which comprises administering to a mammalian specie in need thereof a therapeutically effective amount of a composition of claim 13.

30. A method for treating arthritis which comprises administering to a mammalian specie in need thereof a therapeutically effective amount of a composition of claim 13.

31. A method for treating proliferative diseases which comprises administering to a mammalian specie in need thereof a therapeutically effective amount of a composition of claim 14.

32. A method for treating cancer which comprises administering to a mammalian specie in need thereof a therapeutically effective amount of a composition of claim 14.

33. A method for treating proliferative diseases which comprises administering to a mammalian specie in need thereof a therapeutically effective amount of a composition of claim 15.

34. A method for treating cancer which comprises administering to a mammalian specie in need thereof a therapeutically effective amount of a composition of claim 15.

35. A method for the treatment of a cyclin dependent kinase-associated disorder which comprises administering to a subject in need thereof an amount effective therefor of at least one compound of claim 1.

36. A method for treating chemotherapy-induced alopecia, chemotherapy-induced thrombocytopenia, chemotherapy-induced leukopenia or mucocitis which comprises administering to a mammalian specie in need thereof a therapeutically effective amount of a compound of claim 1.

37. The compound of claim 1 wherein said pharmaceutically acceptable salt is selected from the group consisting of hydrochloride, dihydrochloride, sulfate, trifluoroacetate, mixture of trifluoroacetate and hydrochloride, tartrate, fumarate, succinate, maleate, citrate, methanesulfonate, bromate and iodate salts.

38. The compound of claim 2 wherein said pharmaceutically acceptable salt is selected from the group consisting of hydrochloride, dihydrochloride, sulfate, trifluoroacetate, mixture of trifluoroacetate and hydrochloride, tartrate, fumarate, succinate, maleate, citrate, methanesulfonate, bromate and iodate salts.

39. The compound of claim 3 wherein said pharmaceutically acceptable salt is selected from the group consisting of hydrochloride, dihydrochloride, sulfate, trifluoroacetate, mixture of trifluoroacetate and hydrochloride, tartrate, fumarate, succinate, maleate, citrate, methanesulfonate, bromate and iodate salts.

40. The compound of claim 4 wherein said pharmaceutically acceptable salt is selected from the group consisting of hydrochloride, dihydrochloride, sulfate, trifluoroacetate, mixture of trifluoroacetate and hydrochloride, tartrate, fumarate, succinate, maleate, citrate, methanesulfonate, bromate and iodate salts.

41. The compound of claim 5 wherein said pharmaceutically acceptable salt is selected from the group consisting of hydrochloride, dihydrochloride, sulfate, trifluoroacetate, mixture of trifluoroacetate and hydrochloride, tartate, fumarate, succinate, maleate, citrate, methanesulfonate, bromate and iodate salts.

42. The compound of claim 6 wherein said pharmaceutically acceptable salt is selected from the group consisting of hydrochloride, dihydrochloride, sulfate, trifluoroacetate, mixture of trifluoroacetate and hydrochloride, tartrate, fumarate, succinate, maleate, citrate, methanesulfonate, bromate and iodate salts.

43. The compound of claim 7 wherein said pharmaceutically acceptable salt is selected from the group consisting of hydrochloride, dihydrochloride, sulfate, trifluoroacetate, mixture of trifluoroacetate and hydrochloride, tartrate, fumarate, succinate, maleate, citrate, methanesulfonate, bromate and iodate salts.

44. The compound of claim 8 wherein said pharmaceutically acceptable salt is selected from the group consisting of hydrochloride, dihydrochloride, sulfate, trifluoroacetate, mixture of trifluoroacetate and hydrochloride, tartrate, fumarate, succinate, maleate, citrate, methanesulfonate, bromate and iodate salts.

45. The compound of claim 9 wherein said pharmaceutically acceptable salt is selected from the group consisting of hydrochloride, dihydrochloride, sulfate, trifluoroacetate, mixture of trifluoroacetate and hydrochloride, tartrate, fumarate, succinate, maleate, citrate, methanesulfonate, bromate and iodate salts.

46. The compound of claim 10 wherein said pharmaceutically acceptable salt is selected from the group consisting of hydrochloride, dihydrochloride, sulfate, trifluoroacetate, mixture of trifluoroacetate and hydrochloride, tartrate, fumarate, succinate, maleate, citrate, methanesulfonate, bromate and iodate salts.

47. The compound of claim 11 wherein said pharmaceutically acceptable salt is selected from the group consisting of hydrochloride, dihydrochloride, sulfate, trifluoroacetate, mixture of trifluoroacetate and hydrochloride, tartrate, fumarate, succinate, maleate, citrate, methanesulfonate, bromate and iodate salts.

48. The compound of claim 12 wherein said pharmaceutically acceptable salt is selected from the group consisting of hydrochloride, dihydrochloride, sulfate, trifluoroacetate, mixture of trifluoroacetate and hydrochloride, tartrate, fumarate, succinate, maleate, citrate, methanesulfonate, bromate and iodate salts.

49. The pharmaceutical composition of claim 13 wherein said pharmaceutically acceptable salt is selected from the group consisting of hydrochloride, dihydrochloride, sulfate, trifluoroacetate, mixture of trifluoroacetate and hydrochloride, tartrate, fumarate, succinate, maleate, citrate, methanesulfonate, bromate and iodate salts.

50. The pharmaceutical composition of claim 14 wherein said pharmaceutically acceptable salt is selected from the group consisting of hydrochloride, dihydrochloride, sulfate, trifluoroacetate, mixture of trifluoroacetate and hydrochloride, tartrate, fumarate, succinate, maleate, citrate, methanesulfonate, bromate and iodate salts.

51. The pharmaceutical composition of claim 15 wherein said pharmaceutically acceptable salt is selected from the group consisting of hydrochloride, dihydrochloride, sulfate, trifluoroacetate, mixture of trifluoroacetate and hydrochloride, tartrate, fumarate, succinate, maleate, citrate, methanesulfonate, bromate and iodate salts.

52. The method of claim 17 wherein said pharmaceutically acceptable salt of said compound is selected from the group consisting of hydrochloride, dihydrochloride, sulfate, trifluoroacetate, mixture of trifluoroacetate and hydrochloride, tartrate, fumarate, succinate, maleate, citrate, methanesulfonate, bromate and iodate salts.

53. The method of claim 18 wherein said pharmaceutically acceptable salt of said compound is selected from the group consisting of hydrochloride, dihydrochloride, sulfate, trifluoroacetate, mixture of trifluoroacetate and hydrochloride, tartrate, fumarate, succinate, maleate, citrate, methanesulfonate, bromate and iodate salts.

54. The method of claim 20 wherein said pharmaceutically acceptable salt of said compound is selected from the group consisting of hydrochloride, dihydrochloride, sulfate, trifluoroacetate, mixture of trifluoroacetate and hydrochloride, tartrate, fumarate, succinate, maleate, citrate, methanesulfonate, bromate and iodate salts.

55. The method of claim 27 wherein said pharmaceutically acceptable salt of said compound is selected from the group consisting of hydrochloride, dihydrochloride, sulfate, trifluoroacetate, mixture of trifluoroacetate and hydrochloride, tartrate, fumarate, succinate, maleate, citrate, methanesulfonate, bromate and iodate salts.

56. The method of claim 28 wherein said pharmaceutically acceptable salt of said compound is selected from the group consisting of hydrochloride, dihydrochloride, sulfate, trifluoroacetate, mixture of trifluoroacetate and hydrochloride, tartrate, fumarate, succinate, maleate, citrate, methanesulfonate, bromate and iodate salts.

57. The method of claim 31 wherein said pharmaceutically acceptable salt of said compound is selected from the group consisting of hydrochloride, dihydrochloride, sulfate, trifluoroacetate, mixture of trifluoroacetate and hydrochloride, tartrate, fumarate, succinate, maleate, citrate, methanesulfonate, bromate and iodate salts.

58. The method of claim 32 wherein said pharmaceutically acceptable salt of said compound is selected from the group consisting of hydrochloride, dihydrochloride, sulfate, trifluoroacetate, mixture of trifluoroacetate and hydrochloride, tartrate, fumarate, succinate, maleate, citrate, methanesulfonate, bromate and iodate salts.

59. The method of claim 36 wherein said pharmaceutically acceptable salt of said compound is selected from the group consisting of hydrochloride, dihydrochloride, sulfate, trifluoroacetate, mixture of trifluoroacetate and hydrochloride, tartrate, fumarate, succinate, maleate, citrate, methanesulfonate, bromate and iodate salts.

* * * * *

UNITED STATES PATENT AND TRADEMARK OFFICE
CERTIFICATE OF CORRECTION

PATENT NO. : 6,515,004 B1
DATED : February 4, 2003
INVENTOR(S) : Misra et al.

It is certified that error appears in the above-identified patent and that said Letters Patent is hereby corrected as shown below:

Column 26,
Lines 54 to 56 should read -- N-[5-[[[5-(1,1-Dimethylethyl)-2-oxazolyl]methyl]thio]-2-thiazolyl]-4-piperidinecarboxamide, 0.5-L-tartaric acid salt --

Signed and Sealed this

Seventh Day of September, 2004

JON W. DUDAS
*Director of the United States Patent and Trademark Office*